Figure 1:
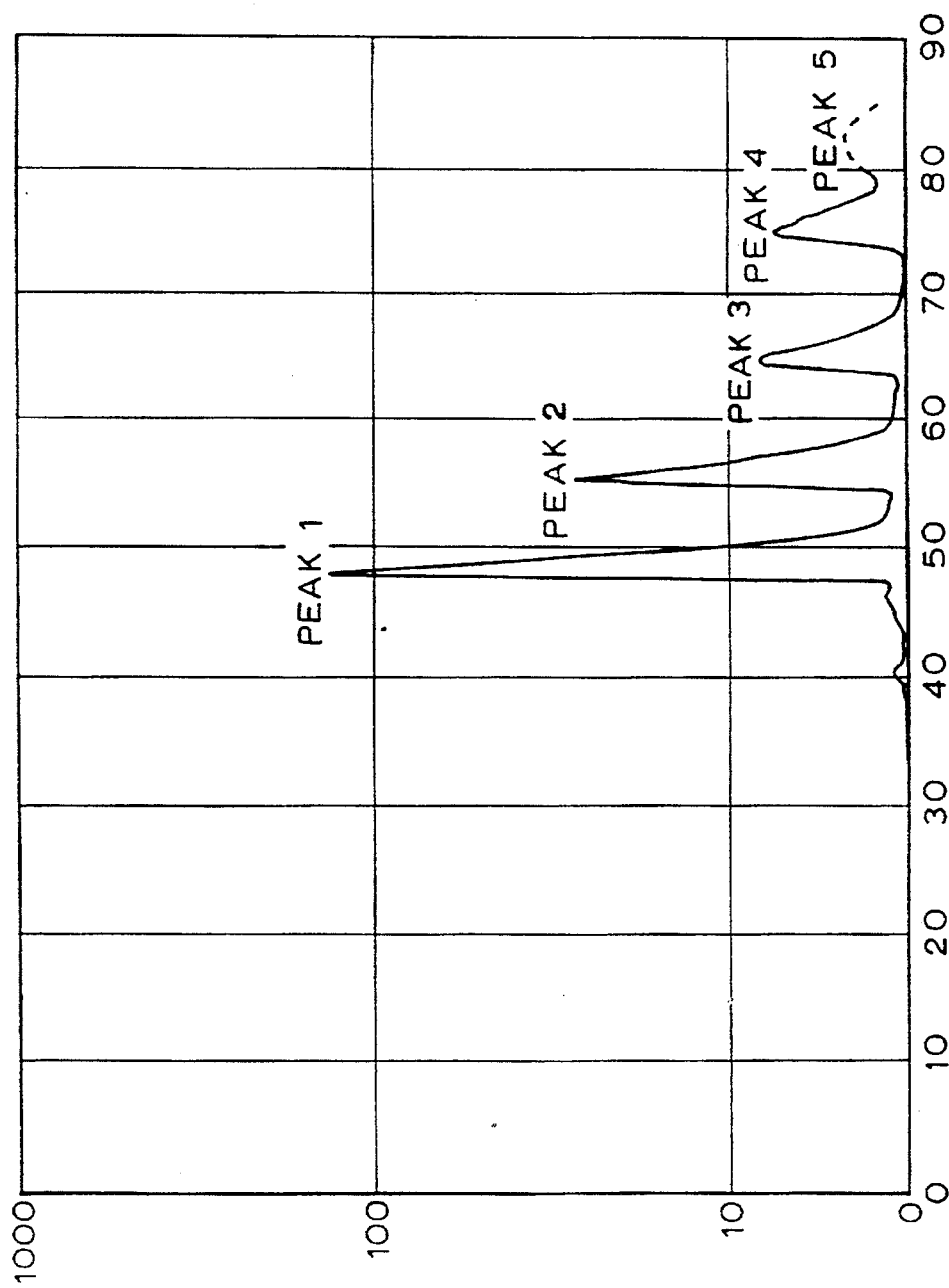

United States Patent [19]

Law

[11] Patent Number: 5,663,074
[45] Date of Patent: Sep. 2, 1997

[54] NUCLEOPHILIC POLYSUBSTITUTED ARYL ACRIDINIUM ESTER CONJUGATES AND SYNTHESES THEREOF

[75] Inventor: Say-Jong Law, Westwood, Mass.

[73] Assignee: Chiron Diagnostics Corporation, Walpole, Mass.

[21] Appl. No.: 32,947

[22] Filed: Mar. 17, 1993

Related U.S. Application Data

[63] Continuation-in-part of Ser. No. 871,601, Apr. 17, 1992, which is a continuation of Ser. No. 249,620, Sep. 26, 1988, abandoned.

[51] Int. Cl.$^6$ .............. G01N 33/533; G01N 33/531; C08H 1/00; C07D 219/08
[52] U.S. Cl. .............. 436/546; 436/543; 436/544; 530/403; 530/404; 530/405; 530/406; 530/408; 530/409; 530/410; 530/411; 546/104
[58] Field of Search .............. 530/403–406, 530/408–411; 436/543–546; 546/104

[56] References Cited

U.S. PATENT DOCUMENTS

| | | | |
|---|---|---|---|
| 3,352,791 | 11/1967 | Sheehan et al. | 252/188.3 |
| 3,689,391 | 9/1972 | Ullman | 204/159 |
| 4,098,876 | 7/1978 | Piasio et al. | 424/1 |
| 4,193,983 | 3/1980 | Ullman et al. | 424/12 |
| 4,244,940 | 1/1981 | Jeong et al. | 424/1 |
| 4,656,129 | 4/1987 | Wagner | 435/7 |
| 4,695,554 | 9/1987 | O'Connell et al. | 436/528 |
| 4,704,355 | 11/1987 | Bernstein | 435/6 |
| 4,745,181 | 5/1988 | Law et al. | 530/391.5 |
| 4,918,192 | 4/1990 | Law et al. | 546/104 |
| 4,933,121 | 6/1990 | Law et al. | 264/4.3 |
| 4,946,958 | 8/1990 | Campbell et al. | 546/104 |
| 4,950,613 | 8/1990 | Arnold et al. | 436/546 |
| 4,978,614 | 12/1990 | Bronstein | 435/21 |
| 5,004,565 | 4/1991 | Schaap | 252/700 |
| 5,094,785 | 3/1992 | Law et al. | 264/4.3 |
| 5,110,932 | 5/1992 | Law et al. | 546/102 |
| 5,241,070 | 8/1993 | Law et al. | 546/107 |

FOREIGN PATENT DOCUMENTS

| | | |
|---|---|---|
| 0144084 | 6/1985 | European Pat. Off. |
| 0216553 | 4/1987 | European Pat. Off. |
| 0257541 | 8/1987 | European Pat. Off. |
| 0263657 | 4/1988 | European Pat. Off. |
| 0322926 | 7/1989 | European Pat. Off. |
| 0324202 | 7/1989 | European Pat. Off. |
| 0330050 | 8/1989 | European Pat. Off. |
| 0361817 | 4/1990 | European Pat. Off. |
| 1461877 | 1/1977 | United Kingdom |

OTHER PUBLICATIONS

Hart et al (1987) J. Immunol Methods 101:91–96.
Seitz (1984) Clin. Biochem. 17:120–5.
Sturgess et al (1986) Clin Chem. 32(3):532–5.
Patel et al (1982) *Luminescent Assays & Perspectives in Endocrinology and Clinical Chemistry* ed by MiSerio et al, Raven Press; NY 1982, pp. 181–189.
Weeks et al (1985) J. Immunol. Methods 80:33–8.
Allen et al., 247 J. Biol Chem 7695 (1972).
Anderson et al., B33 Acta Chemica Scandinavia 695 (1979).
Applied Biosystems, Inc., Foster City, CA, User Manual for DNA/RNA Synthesizer, (1990), iii–vii, 6–1 to 6–21.
Applied Biosystems, Inc., Peptide Synthesizer User's Manual (1988), pp. 0–4 to 0–11, 6–5 to 6–18.
Clontech Laboratories, Inc., Palo Alto, CA, User Manual on DNA Modification Reagents for Use in Automated DNA Synthesis, pp. 2–3.
Hammond et al., 6 J. Biolum and Chemilum., 35–43 (1991).
Hendrickson et al., Organic Chemistry, 3d. ed., McGraw Hill, NY (1970), p. 71.
Kricka, L. and Carter T., Clinical and Biochemical Luminescence, pp. 153–178 (Marcel Dekker, Inc., N.Y. and Basel, 1982).
March, Advanced Organic Chemistry, 3d. ed., John Wiley & Sons, NY (1985), pp. 304–310, 587.
Martinet et al., Bull Soc Chim Fr., vol. 45 pp. 101–109 (1929).
Mayer et al., "Hydrophilic Acridinium–9–Carboxylic Acid Derivatives Used as Labels in Luminescent Assays" in Stanley et al. Eds., p. 99 (1991, Wiley, Chichester).
Meek et al., 11 J. Chem & Eng Data, vol. 14, pp. 388–391 (1969).
Miller et al., 25 Ann Clin Biochem 27–34 (1988).
Patel et al., 97 CA 85407p (1982).
Richardson et al., 31/10 Clin Chem 1664–8 (1985).
Weeks et al., 29 Clin Chem 1474 (1983).

*Primary Examiner*—Michael P. Woodward
*Attorney, Agent, or Firm*—Arthur S. Morgenstern; Robert P. Blackburn; Maurice M. Klee

[57] ABSTRACT

This invention is directed to novel nucleophilic polysubstituted aryl acridinium conjugates and the methods for preparation thereof. The novel nucleophilic polysubstituted aryl acridinium conjugates are useful in biological assays, including novel assays for the determination of Vitamin $B_{12}$, folate, cortisol, estradiol, and thromboxane $B_2$.

53 Claims, 15 Drawing Sheets

2

NUCLEOPHILIC POLYSUBSTITUTED ARYL ACRIDINIUM ESTER CONJUGATES AND SYNTHESES THEREOF

This application is a continuation in part of Ser. No. 07/871,601 filed Apr. 17, 1992, which is a continuation of Ser. No. 07/249,620 filed Sep. 26, 1988, now abandoned.

FIELD OF THE INVENTION

This invention relates to novel nucleophilic polysubstituted aryl acridinium esters. This invention also relates to conjugates formed from the novel nucleophilic polysubstituted aryl acridinium esters. This invention further relates to assays utilizing the novel nucleophilic polysubstituted aryl acridinium esters and conjugates thereof.

BACKGROUND OF THE INVENTION

The use of acridinium esters as chemiluminescent labels in clinical assays is known. For example, European Patent Application No. 82306557.8 describes the use of an aryl acridinium ester linked to an N-succinimidyl moiety as a chemiluminescent label in immunoassays. U.S. Pat. No. 4,745,181 and U.S. patent application Ser. No. 133,792, filed Dec. 14, 1987, now U.S. Pat. No. 4,918,192 describe polysubstituted aryl acridinium esters which are useful in immunoassays and nucleic acid hybridization assays. U.S. patent application Ser. No. 226,639, filed on Aug. 1, 1988, describes hydrophilic polysubstituted aryl acridinium esters and conjugates thereof useful in clinical assays, particularly those assays involving liposomes.

Richardson et al (Clin. Chem. 31/10, 1664–1668, 1985) and Miller et al (Ann. Clin. Biochem 25, 27–34, 1988) describe the use of 4-(2-aminoethyl)phenyl acridine-9-carboxylate in a chemiluminescent immunoassay for plasma progesterone.

However, the prior art acridinium esters often cannot effectively form conjugates with certain analytes. These analytes may lack nucleophilic groups or may contain carboxylic groups which are not readily amenable to modifications. In some cases, the nucleophilic group of the analyte cannot be acylated with an active-group containing acridinium ester because of the resulting deleterious effect on the immunoactivity of the analyte.

The acridine ester of Richardson et al and Miller et al cannot be converted to a useful acridinium ester without the concurrent loss of the nucleophilicity of the ester. The acridine ester must be conjugated first with the target analyte through a nucleophilic reaction, and then subsequently converted to an acridinium ester moiety. The general reaction conditions of the acridine ester-to-acridinium ester conversion are non-selective. As a result, susceptible groups on the target analytes are frequently affected, resulting in the loss of or reduction of the immunoactivity of the resulting conjugate.

Accordingly, it is the purpose of the present invention to provide novel nucleophilic polysubstituted aryl acridinium esters. It is also a purpose of the present invention to provide novel nucleophilic polysubstituted aryl acridinium esters which contain an additional ionizable group.

It is a further purpose of this invention to provide conjugates formed from the novel nucleophilic polysubstituted aryl acridinium esters.

It is a still further purpose of this invention to provide assays utilizing the novel nucleophilic polysubstituted aryl acridinium esters and conjugates thereof.

DESCRIPTION OF THE INVENTION

This invention relates to nucleophilic polysubstituted aryl acridinium esters of the formula:

wherein $R_1$ is alkyl, alkenyl, alkynyl, aryl, or aralkyl containing from 0 to 20 heteroatoms, preferably nitrogen, oxygen, phosphorous, or sulfur;

$R_2$, $R_3$, $R_5$, and $R_7$ are hydrogen, amino, alkoxyl (—OR), hydroxyl, —COOH, halide, nitro,

—CN, —SO₃H, —NHCR, —CR, —COR,
             ‖    ‖    ‖
             O    O    O

—CNHR, —SCN, —R, —SR, or —SSR,
 ‖
 O wherein R is alkyl, alkenyl, alkynyl, aryl, or aralkyl, containing from 0–20 heteroatoms;

$R_4$ and $R_8$ are alkyl, alkenyl, alkynyl, aralkyl, or alkoxyl;

X is an anion, preferably $CH_3SO_4^-$, $FSO_3^-$, halide, $CF_3SO_3^-$, $C_4F_9SO_3^-$, or

-OSO₂—⟨ ⟩—CH₃;

and $R_6$ is:

I
      |
Q—R—Nu, Q—R—Nu, or Q—Nu wherein Q is

—O—, —S—, —NH—,

—C—, —NHCNH—, —NHCNH—,
 ‖     ‖          ‖
 O     S          O

—NHCO—, —NHC—, —CNH—, diazo, or —NHC—;
  ‖       ‖      ‖                ‖
  O       O      O               ⁺NH₂

R is as defined above; I is —SO₃H, —OSO₃H, —PO(OH)₂, —OPO(OH)₂, or —COOH; and Nu is a nucleophilic group.

A nucleophilic group for the purpose of this invention is defined as a chemical group which is electron rich, has an unshared pair of electrons acting as a reactive site, and seeks a positively charged or electron-deficient site on another molecule. Examples of useful nucleophilic groups include amino, hydroxyl, sulfhydryl, or an active methylene group, adjacent to a strong electron-withdrawing group. A strong electron-withdrawing group is defined as a chemical group or substituent which strongly attracts electrons and, therefore, intensifies the positive charge of the carbon atom (or carbonium ion) or nullifies the negative charge of the carbon atom (or carbanion), to which the group is attached. Examples of strong electron-withdrawing groups include —$NO_2$, —CN, —$SO_3H$, —$N(R)_3^+$, —$S(R)_2^+$, and —$NH_3^+$, wherein R is as defined above.

Organic metallic moieties are also useful nucleophilic groups for the purposes of this invention. An organic metallic moiety is defined as an organic moiety comprising carbon-metal bonds. Examples of organic metallic moieties include Grignard reagents, lithium compounds, and phenyl-sodium.

Preferably $R_1$ is alkyl, alkenyl, alkynyl, aryl, or aralkyl of from 1 to 24 carbon atoms;

$R_2$, $R_3$, $R_5$, and $R_7$ are hydrogen, amino, —COOH, —CN, hydroxyl, alkoxyl of from 1 to 4 carbon atoms, nitro, halide, —$SO_3H$, or —SCN;

$R_4$ and $R_8$ are alkyl, alkenyl, alkynyl, or alkoxyl, of from 1 to 8 carbon atoms; and X is halide.

More preferably, $R_1$ is alkyl of from 1 to 10 carbon atoms; $R_2$, $R_3$, $R_5$, and $R_7$ are hydrogen, nitro, —CN, halide, alkoxyl of from 1 to 4 carbon atoms, amino, or —$SO_3H$; and $R_4$ and $R_8$ are alkyl of from 1 to 4 carbon atoms.

Most preferably, $R_1$, $R_4$, and $R_8$ are methyl; $R_2$, $R_3$, $R_5$, and $R_7$ are hydrogen; X is bromide; and $R_6$ is —CONH—$CH_2CH_2$—$NH_2$ or

The $R_5$ and $R_6$ position can be interchanged in the acridinium esters of this invention. Accordingly, the preferred acridinium esters of this invention include acridinium esters of the following formula:

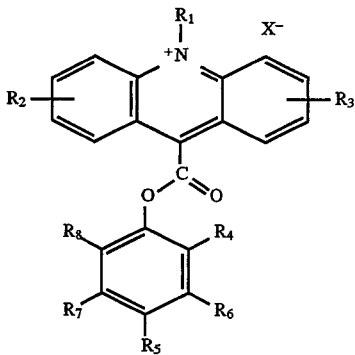

wherein $R_1$, $R_2$, $R_3$, $R_4$, $R_5$, $R_6$, $R_7$, $R_8$, and X are as defined above.

In the foregoing, the aryl or ar portion of aralkyl can be, for example, a substituted or unsubstituted heterocyclic ring or ring system containing from 2 to 20 heteroatoms selected from nitrogen, oxygen, phosphorous and sulfur. For example, the heterocyclic ring or ring system can be selected from the group consisting of 2-pyrimidinyl, 8-purinyl, 2-quinolyl, 2-pteridinyl, 3-isothiazolyl, 2-phenothiazinyl, 3-isoxazoyl, 2-imidazolyl, and 3'-phospho-5-northymidinyl.

This invention also relates to conjugates comprising the above-described acridinium esters of this invention covalently bound to any compound which can covalently bind to the Nu group of the acridinium ester. To form a useful conjugate, the compound must contain at least one functional group capable of binding to the Nu group of the acridinium ester. Preferably, the conjugates are formed from compounds having biological activity, such as proteins, nucleic acids, antigens, haptens, etc.

If Nu is $NH_2$, for example, examples of suitable compounds for forming conjugates of this invention include those compounds which contain functional groups capable of binding with —$NH_2$, such as:

(1) carboxylate groups, as in, e.g., folic acid, carboxylated Vitamin $B_{12}$, Vitamin $B_{12}$-hemisuccinate at the ribose moiety, N-hemisuccinates of $T_4$-methyl ester and $T_3$ methyl ester, thromboxane $B_2$, carboxypropyltheophylline, penicillins, cortisol-3-carboxylmethyloxime, estradiol-6-carboxymethyloxime, morphine-6-hemisuccinate, and the like; (2) ketone groups, as in, e.g., 3-ketodigoxigenine; (3) aldehyde groups, as in, e.g., digoxin-dialdehyde and bromouridine dialdehyde; (4) halides, as in, e.g., dinitroflurobenzene and chlorotriazine derivatives of haptens and proteins; (5) active esters, as in, e.g., N-hydroxysuccinimide and imidate derivatives of haptens and proteins; (6) isocyanate and thioisocyanate, as in, e.g., hapten and protein derivatives.

If Nu is —SH, examples of suitable compounds will contain functional groups capable of binding with —SH, such as maleimido, dithiopyridino, or olefin as found in, e.g., hapten and protein derivatives.

If Nu is —OH, examples of suitable compounds for forming the conjugates of this invention include those compounds which contain functional groups capable of binding with —OH, such as oxirane, as found in, e.g., hapten and protein derivatives.

If Nu is a Grignard moiety or other organo-metallic moiety, examples of suitable compounds for forming the conjugates of this invention include those compounds which contain functional groups capable of binding to the moiety, such as ketone and aldehyde, as found in, e.g., aprotic haptens.

It will be appreciated that numerous other suitable Nu groups can be utilized in the acridinium esters of this invention. It is left for the artisan to choose, which combination of acridinium ester and conjugating compound best serves the needs of the desired application.

The term "activation" (or activate) for the purposes of the specification and the claims means a modification of an existing functional group of a particular compound, which modification generates (or introduces) a new reactive functional group from the prior existing functional group, which new reactive functional group is capable of binding to a target functional group of a second compound. For example, the carboxylic group (—COOH) in thromboxane $B_2$ (see structure below) can be "activated" to produce a mixed anhydride group

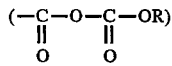

using known procedures in the art. The mixed anhydride can then react with the amino group (—$NH_2$), for example, of 2', 6'-dimethyl-4'-[N-(2 aminoethyl)carbomoyl]phenyl 10-methylacridinium-9-carboxylate bromide (DMAE-ED), to form an amide linkage

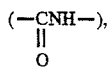

resulting in the formation of a Thromboxane $B_2$-DMAE-ED conjugate (see Example 11 below). As an additional example, the free amino group (—$NH_2$) group on the surface of alkyl siloxane-coated paramagnetic particles (PMP) (Advanced Magnetics Inc., Cambridge, Mass.) can be "activated" by derivatization with homobifunctional glutaraldehyde

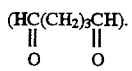

One reactive aldehyde group of the glutaraldehyde covalently binds to the PMP by formation of a Schiff base with the free amino group. The second reactive aldehyde group can then bind with a protein.

The preparation of the conjugates of this invention will vary depending on the acridinium ester and conjugating compound chosen. For example, the following discussion will highlight certain exemplary approaches to forming conjugates from certain compounds and certain preferred Nu groups on the acridinium esters of this invention: (1) when Nu is —$NH_2$ and the conjugating compound contains a carboxylic group, the carboxylic acid group is first activated to form an active ester, such as N-hydroxysuccinimide ester, mixed anhydride, or acyl halide. The activated compound is then reacted with the acridinium ester to form the conjugate; (2) when Nu is —$NH_2$ and the conjugating compound contains a ketone or aldehyde group, the acridinium ester can be directly reacted with the compound to form a Schiff base. The conjugate can then be reacted with a hydride reducing agent, such as sodium cyanoborohydride, to stabilize the linkage; (3) when Nu is —$NH_2$, the acridinium ester can be reacted directly with a conjugating compound containing a reactive group like halide, isocyanate, or thioisocyanate; (4) when Nu is —SH, the conjugating compound should contain a thiol (sulfhydryl)-reactive group, such as maleimido, dithiopyridino, or olefin, to effectively react with the acridinium ester to form a conjugate; (5) when Nu is —OH, it is preferred that the desired conjugating compound contain an oxirane group to effectively react with the acridinium ester to form a conjugate; (6) when Nu is a Grignard or other organo-metallic moiety, the acridinium ester containing such a moiety should be prepared fresh for each use and then reacted with a conjugating compound containing a ketone or aldehyde functional group to form the conjugate.

It will be appreciated that the discussion above is not exhaustive and that numerous other conjugates can be formed from the novel acridinium esters of this invention using known procedures in the art.

The conjugates of this invention are useful as luminescent tracers. The conjugates are particularly useful in luminescent assays using specific binding phenomena such as antibody/antigen immunological reactions, nucleic acid hybridization reactions, or ligand/binding protein interactions.

In one embodiment of the present invention, conjugates are prepared using the acridinium esters of this invention and folate or folate derivatives. Preferably, the acridinium ester used contains both nucleophilic and hydrophilic groups. Preparation of this folate-acridinium ester conjugate involves incubating the acridinium ester with a protected folate intermediate of the following formula (which can be activated at one or both of its carboxylic groups):

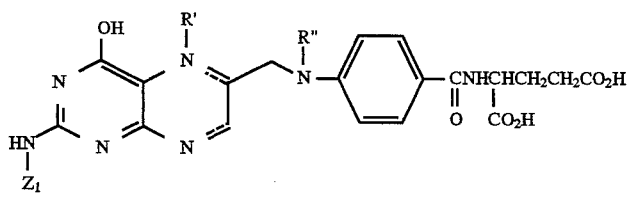

wherein R' is an optional branched or straight-chain, saturated or unsaturated, alkyl of from 1 to 24 carbon atoms, containing 0–20 heteroatoms, preferably nitrogen, oxygen, phosphorous, or sulfur. R" is $Z_2$, hydrogen, or a branched or straight-chain, saturated or unsaturated, alkyl of from 1 to 24 carbon atoms, containing 0–20 heteroatoms, preferably nitrogen, oxygen, phosphorous, or sulfur. The dotted lines are optional double bonds.

$Z_1$ and $Z_2$ are protecting groups. $Z_2$ is optional. The protecting groups can be any group which can protect the primary and secondary amines from reacting with the activated carboxylic group of the folate either intra- or intermolecularly. The protecting groups must be removable under conditions which do not deleteriously affect the acridinium ester, preferably in an acidic environment. Useful pretecting groups include trifluoroacetyl or t-butyloxycarbonyl groups.

After conjugation of the protected folate intermediate with the acridinium ester, the folate moiety is deblocked by removal of the protecting groups. This deblocking is preferably conducted in an acidic environment using an acidic media such as HBr/acetic acid, which is capable of removing the protecting groups without destroying the integrity of the conjugate. The conjugate so formed can then be used as a tracer in an assay for measuring folates.

In another embodiment of this invention, conjugates are formed using the acridinium esters of this invention and Vitamin $B_{12}$ (cyanocobalamin). Vitamin $B_{12}$ has the following structure:

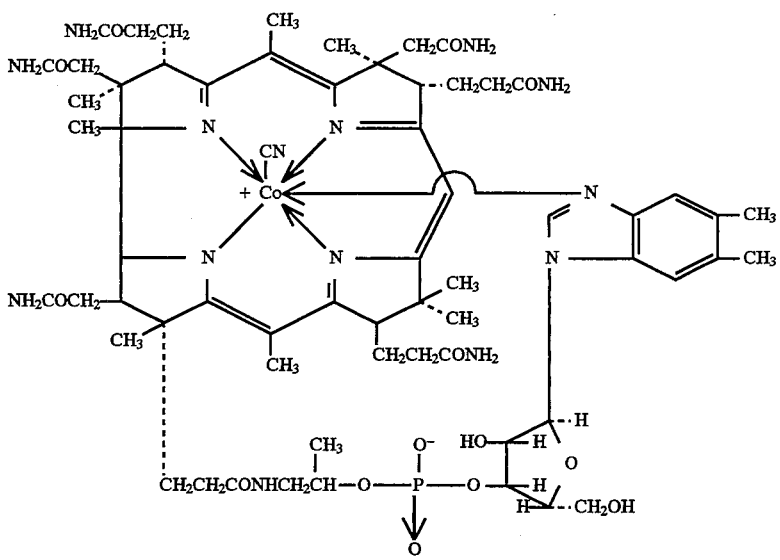

Treating Vitamin $B_{12}$ with dilute acid will deaminate 1, 2 and/or 3 of the primary propanamide side chains of the Corrin ring to generate a carboxylic function. This carboxylate function is then used to conjugate the Vitamin $B_{12}$ to the nucleophilic acridinium esters of this invention.

The ratio of monocarboxylic Vitamin $B_{12}$ (one carboxylate function), dicarboxylic Vitamin $B_{12}$ (two carboxylate functions), and tricarboxylic Vitamin $B_{12}$ (three carboxylate functions) will depend on the acid concentration and the reaction time. Monocarboxylic Vitamin $B_{12}$ is the desired product for the purpose of preparing the conjugates of this invention. Typically, by optimizing known procedures, such as the procedure described in Allen et al, J. Biol. Chem. 247, 7695 (1972), mixtures of mono-, di-, and tricarboxylic Vitamin $B_{12}$ can be generated which contain up to 40% monocarboxylic Vitamin $B_{12}$ (see FIGS. 3 and 4). Prior art procedures utilize a strong anion exchanger to separate the monocarboxylic Vitamin $B_{12}$ from the di- and tricarboxylic Vitamin $B_{12}$. [Allen et al, J. Biol. Chem. 247, 7695, 1972.)

There are potentially three forms of monocarboxyiic Vitamin $B_{12}$, depending on which of the 3 primary propanamide side chains have been deaminated. It is desirable to separate these three monocarboxylic Vitamin $B_{12}$ forms.

It has been unexpectedly discovered that by separating the mixture of carboxylated Vitamin $B_{12}$ on Reverse Phase High Perfomance Liquid Chromatography (HPLC), the monocarboxylic Vitamin $B_{12}$ forms can be separated and isolated from the di- and tri-carboxylic forms and from each other. Accordingly, this allows the artisan to obtain individual monocarboxylic Vitamin $B_{12}$ forms with high purity without the preliminary ion-exchange fractionation step of the prior art.

It has also been unexpectedly discovered that one monocarboxylic Vitamin $B_{12}$ form is more effective than the other two forms in the conjugates of this invention for use in Vitamin $B_{12}$ assays.

In a further embodiment of this invention, conjugates are formed using the acridinium esters of this invention and estradiol. These conjugates can be used, for example, as tracers in assays for 17-beta-estradiol.

17-beta-estradiol has the following structure:

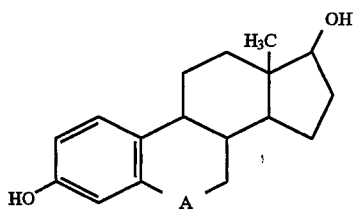

wherein A is $CH_2$. Useful derivatives of 17-beta-estradiol include 6-keto-17-beta-estradiol (where A is

)

and, preferably, 6-carboxymethyloxime-17-beta-estradiol (where A is

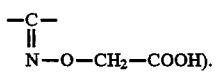

).

Conjugation with an appropriate acridinium ester of this invention can occur at any of the available functional groups on the 17-beta-estradiol or derivative therefore, i.e., the phenolic 3-OH group, the secondary 17-OH group, or the keto or the carboxymethyloxime group created at the C-6 position. The choice of functional group for conjugation will depend generally on such factors as compatibility with the desired immunoassay system, the stability of conjugate prepared, and the ease of preparation. Preferably the conjugate is prepared by activating the carboxylic group of 6-carboxymethyloxime-17-beta-estradiol and then reacting the activated estradiol derivative with an appropriate acridinium ester of the invention. The resulting conjugate can then be used as a tracer in an assay for determining 17-beta-estradiol.

The acridinium esters of this invention can also be used to form useful conjugates with cortisol. Cortisol has the following structure:

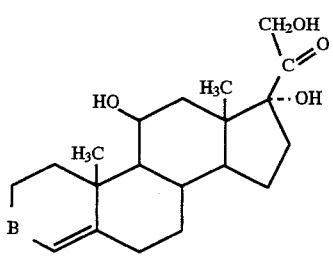

wherein B is

A derivative of cortisol is 3-carboxymethyloxime cortisol (where B is

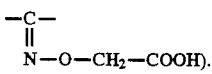

Conjugation with an appropriate acridinium ester of this invention can occur at any of the available functional groups on the cortisol or derivative thereof, i.e., the 21-OH group, the 17-OH group, the 11-OH group, the 20-keto group, the 3-keto group, and the 3-carboxymethyloxime group. Preferably, the conjugate is prepared by activating the carboxylic group of the 3-carboxymethyloxime cortisol and then reacting the activated cortisol derivative with an appropriate acridinium ester of this invention. The resulting tracer can then be used as a tracer in an assay for cortisol.

Useful conjugates can be formed between the acridinium esters of this invention and thromboxane $B_2$ and other prostaglandin analogs. Thromboxane $B_{12}$ has the following structure:

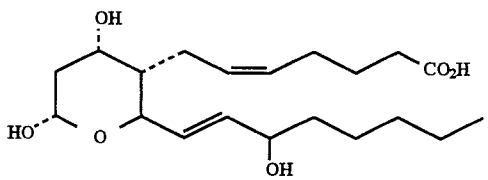

Conjugation with an appropriate acridinium ester of this invention can occur at any of the three hydroxyl groups or the olefin functional groups. The choice of functional group will depend generally on such factors as compatibility with a specific binding protein, and low cross reactivity with non-target prostaglandin analogs. Preferably, the conjugate is prepared by activating the terminal carboxylic group of the thromboxane $B_2$ and then reacting the resulting thromboxane $B_2$ derivative with an appropriate acridinium ester of this invention. The resulting conjugate can then be used as a tracer in assays for thromboxane $B_2$.

This invention also relates to assays utilizing the conjugates of this invention as chemiluminescent tracer compounds. The assays can be homogeneous or heterogeneous. The assays can be competitive inhibition assays where, for example, the analyte to be determined is a univalent hapten molecule. The assays can also be non-competititve, such as sandwich assays where, for example, the acridinium esters of this invention are conjugated to an antibody or a receptor molecule. The components or reagents of the assays utilizing the conjugates of this invention can be mixed together in any desired manner or sequence provided that the resultant acridinium ester label can be measured in a subsequent detection system. Accordingly, the assays utilizing the conjugates of this invention can be conducted in a forward mode, reverse mode, or a simultaneous mode (see, e.g., U.S. Pat. Nos. 4,098,876 and 4,244,940).

Assays for the detection and measurement of Vitamin $B_{12}$ and folate are illustrative of the assays which can be conducted using the conjugates of this invention. Such assays can use the Vitamin $B_{12}$-acridinium ester or the folate-acridinium ester conjugates of this invention. A general discussion of radioisotope dilution assays for Vitamin $B_{12}$ and for folate is found in U.S. Pat. No. 4,451,571, herein incorporated by reference.

Assays for the detection or measurement of Vitamin $B_{12}$ or folate in a sample generally require a sample preparation step wherein the Vitamin $B_{12}$ or folate in the sample is released (liberated) from endogenous binding proteins. Methods to release the Vitamin $B_{12}$ or folate from the respective binding proteins include heating or boiling the sample, or using a chemical releasing agent. Typical releasing agents comprise a strong base, such as NaOH. A sulfhydryl compound, such as dithiothreitol (DTT) or beta-mercaptoethanol, is also typically added during the sample preparation step. The sulfhydryl compound can be added before, after, or along with, the addition of the releasing agent.

In one assay for Vitamin $B_{12}$, following the sample preparation step, the Vitamin $B_{12}$ tracer compound is combined with the sample and purified hog intrinsic factor (HIF) immobilized on a solid phase. The sample and tracer compound compete for binding sites on the HIF. The amount of tracer compound bound to HIF is inversely proportional to the amount of Vitamin $B_{12}$ in the sample.

In one assay for folate, following the sample preparation step, the folate tracer compound is combined with the sample and bovine lactoglobulin or folate binding protein (FBP), immobilized on a solid phase. The sample and tracer compound compete for binding sites on the FBP. The amount of tracer compound bound to FBP is inversely proportional to the amount of folate in the sample.

It has been discovered that the sulfhydryl compounds used in the sample preparation step remain in the solid phase at the time of counting (i.e., measuring the amount of label associated with the solid phase). The presence of varying concentrations of the sulfhydryl compound (particularly DTT) in the solid phase can quench the photon output of the chemiluminescent reaction of the acridinium ester label and result in poor assay precision and reduced signal. It was unexpectedly discovered that by incubating the solid phase in a solution comprising a thiol-reactive compound, such as ethyl maleimide, prior to counting, the quenching effect of the sulfhydryl compound is reduced or eliminated. Preferably, the concentration of the thiol-reactive compound in the solution is about 0.01 mM to about 50 mM, more preferably about 0.5 mM to about 10 mM, and most preferably, about 1 mM.

The following Examples illustrate the present invention.

EXAMPLE 1

Preparation of 2', 6'-Dimethyl-4'-[N-(2-aminoethyl) carbomoyl]phenyl 10-methylacridinium-9-carboxylate bromide (DMAE-ED)

A solution of 2', 6'-dimethyl-4'-carboxylphenyl 10-methylacridinium-9-carboxylate bromide (DMAE, 200 mg, 0.43 mmole) (see copending U.S. application Ser. No. 226,639, filed on Aug. 1, 1988) in 30 ml of dimethylformamide (DMF) was cooled in ice bath, treated with triethylamine (0.25 ml, 1.72 mmole), ethylchloroformate (0.08 ml, 0.85 mmole) and 30 ml of chloroform to form a reaction mixture. After 20 min. of stirring, the reaction mixture was transferred to a dried dropping funnel and added dropwise over a 15 minute period to a solution of ethylenediamine in 10 ml of DMF/CHCl$_3$ (1:1) to form a second reaction mixture.

The second reaction mixture was then stirred at room temperature overnight and then evaporated to dryness under vacuo. The residue produced from the evaporation was taken up in 3–4 ml of chloroform/methanol/water (65:25:4), purified on two 20×20 cm preparative thin layer chromatography TLC plates (Silica gel 60, F254, Merck & Co., Inc., Rahway, N.J.) and developed with the same solvent system. The yellow major band which developed (Rf=0.47) (which could also be detected under long and short UV light) was stripped and eluted with the same solvent system. The eluent was then evaporated. The residue from this evaporation was triturated with 30 ml of 10% methanol/chloroform and filtered through Whatman #1 filter paper under gravity. The filtrate so produced was evaporated to produce DMAE-ED (110 mg, 50%). Fast Atom Bombardment (FAB) Mass Spectral Analysis (performed by Oneida Research Services, Whitesboro, N.Y.) in the positive ion mode gave a M+ peak of 428. Isotopic bromide peaks 79 and 81 of about equal intensity were detected in the negative ion mode.

EXAMPLE 2

Preparation of N-tert-Butyloxycarbonyl-S-(3-sulfopropyl) cysteine (BOC-SulfoCys)

2-(tert-butoxycarbonyloxyimino)-2-phenylacetonitrile (BOC-ON) (121 mg, 0.49 mmole) (Aldrich Chem. Co., Milwaukee, Wis.) was added to a solution of S-(3-sulfopropyl)cysteine (SulfoCys, 100 mg, 0.41 mmole), (prepared by the method of U. T. Ruegg and J. Rudinger, J. Peptide Protein Res. 6, 447, 1974), and triethylamine (0.18 ml, 1.23 mmole) in 3 ml of 50% aqueous dioxane to form a reaction mixture. The reaction mixture was heated at 50°–55° C. for 1 hour to obtain a yellow solution. The reaction mixture was then cooled, diluted with 5 ml of water, and washed with ethylacetate (3×10 ml). The resultant aqueous layer was evaporated to dryness under vacuo by coevaporating with methanol twice. TLC (Silica gel 60, Merck & Co., Inc.) analysis of the residue produced by the evaporation, using a solvent system of chloroform/methanol/water (55:40:5), showed complete conversion of SulfoCys to BOC-SulfoCys.

EXAMPLE 3

Preparation of 2', 6'-Dimethyl-4'-{N-[N-(2-tert-butyloxycarbonylamino-3-S-(3'-sulfopropyl)-thiopropionyl)-2-aminoethyl]carbamoyl-}phenyl 10-methylacridinium-9-carboxylate bromide (BOC-SulfoCys-ED-DMAE)

A solution of BOC-SulfoCys (3.42 mmole) (Example 2), and DMAE-ED (400 mg, 0.79 mmole) (Example 1) in 110 ml of DMF/CHCl$_3$ (1:1) was treated with dicyclohexylcarbodiimide (325 mg, 1.57 mmole), stirred at room temperature for 3 hours and evaporated to dryness. The residue from the evaporation was taken up in about 15 ml of chloroform/methanol/water (65:25:4) and purified on 8 preparative TLC plates (Silica gel 60, Merck & Co., Inc.) developed with the same solvent system.

The major yellow band which developed at about Rf of 0.55 was stripped and eluted with the same solvent system.

The eluent was then evaporated to dryness under vacuo to produce BOC-SulfoCys-ED-DMAE (630 mg, 90%)

EXAMPLE 4

Preparation of 2', 6'-Dimethyl-4'-{N-[N-(2-amino-3-S-(3'-sulfopropyl)-thiopropionyl)-2-aminoethyl] carbamoyl}phenyl 10-methylacridinium-9-carboxylate bromide (SulfoCys-ED-DMAE)

A solution of BOC-SulfoCys-ED-DMAE (630 mg, 0.715 mmole) (Example 3) in 4 ml of 36% HBr/Acetic acid was kept at room temperature for 5 hours to form a reaction mixture. The reaction mixture was added dropwise to about 30 ml of anhydrous ethylether, forming a gummy precipitate and supernatant. The supernatant was removed from the precipitate. The precipitate was then dissolved in about 10 ml of methanol and the resultant solution was then added dropwise to about 30 ml of fresh anhydrous ethylether, forming a yellow precipitate and supernatant.

The yellow precipitate and supernatant were then filtered through a medium porosity frit and the resultant yellow solid residue was then washed with anhydrous ethylether, and then air dried to produce SulfoCys-ED-DMAE (438 mg, 93.7%).

FAB Mass Spectral analysis (performed by both Oneida Research Services, Whitesboro, N.Y. and Institute of Chemical Analysis, Northeastern University, Boston, Mass.) in the positive ion mode gave a M+ peak of 653.

EXAMPLE 5

Preparation of Monocarboxylic Vitamin $B_{12}$

A. Preparation of Deaminated Vitamin $B_{12}$

Vitamin $B_{12}$ (1.0 g, 0.738 mmole) (Sigma Chemicals, St. Louis, Mo.) was added to 80 ml of 0.5N HCl to form a reaction mixture and stirred at room temperature for 65 hours. The reaction mixture was then loaded onto a 4×15 cm column of Bio-Rad AG1-X8 (acetate form) (Bio-Rad Laboratories, Richmond, Calif.), 100–200 mesh, packed and eluted as described in Allen, R. H. and Majerus, P. W., J. Biological Chem., 247, 7695–7701 (1972). The initial 300 ml of red eluent was collected and evaporated to dryness under vacuum to produce about 1 gram of a mixture of mono-, di-, and tricarboxylated Vitamin $B_{12}$.

B. Preparation of Mixture of Mono-carboxylated Vitamin $B_{12}$

The mixture of carboxylated Vitamin $B_{12}$ prepared in A was fractionated by QAE-Sephadex A-25 chromatography to obtain a mixture of monocarboxylated Vitamin $B_{12}$ as described by Allen et al. (J. Biol. Chem. 247, 7695, 1972).

C. Preparative HPLC for the Separation of the Carboxylated Vitamin $B_{12}$ 50 mg of the mixture of the mono-, di-, and tri-carboxylated Vitamin $B_{12}$ from A in 2 ml of water was injected into a Waters Delta-Prep 3000 HPLC system (Waters Associates, Milford, Mass.) with an ISCO-Foxy fraction collector, an ISCO-2150 peak separator (ISCO, Lincoln, Nebr.) and a YMC AP 363-15, 30 mm×25 cm stainless steel column packed with C18-bonded silica of 15 um particles, spherical shape, and 300A pore size (YMC, Inc., Morris Plains, N.J.).

The carboxylated Vitamin $B_{12}$ was eluted from the column for each run using acetonitrile as Solvent B and 0.05M triethylammonium acetate, pH 4.5, as Solvent A, in the following manner:

1. Run 1—step-gradient elution:

20 min. on 8% Solvent B/92% Solvent A then
10 min. on 10% Solvent B/90% Solvent A then
50 min. on 15% Solvent B/85% Solvent A 2. Run 2—isocratic elation:
   Using 15% Solvent B/85% Solvent A
3. Run 3—step-gradient elution:
   10 min. on 10% Solvent B/90% Solvent A
   30 min. on 15% Solvent B/85% Solvent A
4. Run 4—isocratic elution:
   10% Solvent B/90% Solvent A The flow rate of the column was 20 ml/min. for each run and the eluted materials were detected at a wavelength of 280 nm.

FIG. 1 is a profile of the separation of the mixture of carboxylated Vitamin $B_{12}$ obtained in Run 1. Five peaks were collected although Peak 5 was not recorded because the preprogrammed recording time ended prior to elution of Peak 5.

Peak 5 was determined based on the characteristic red color of the fraction collected. Peak 5 was then added to the graph as a dotted line peak indicating its location had it been recorded.

Figure 2:
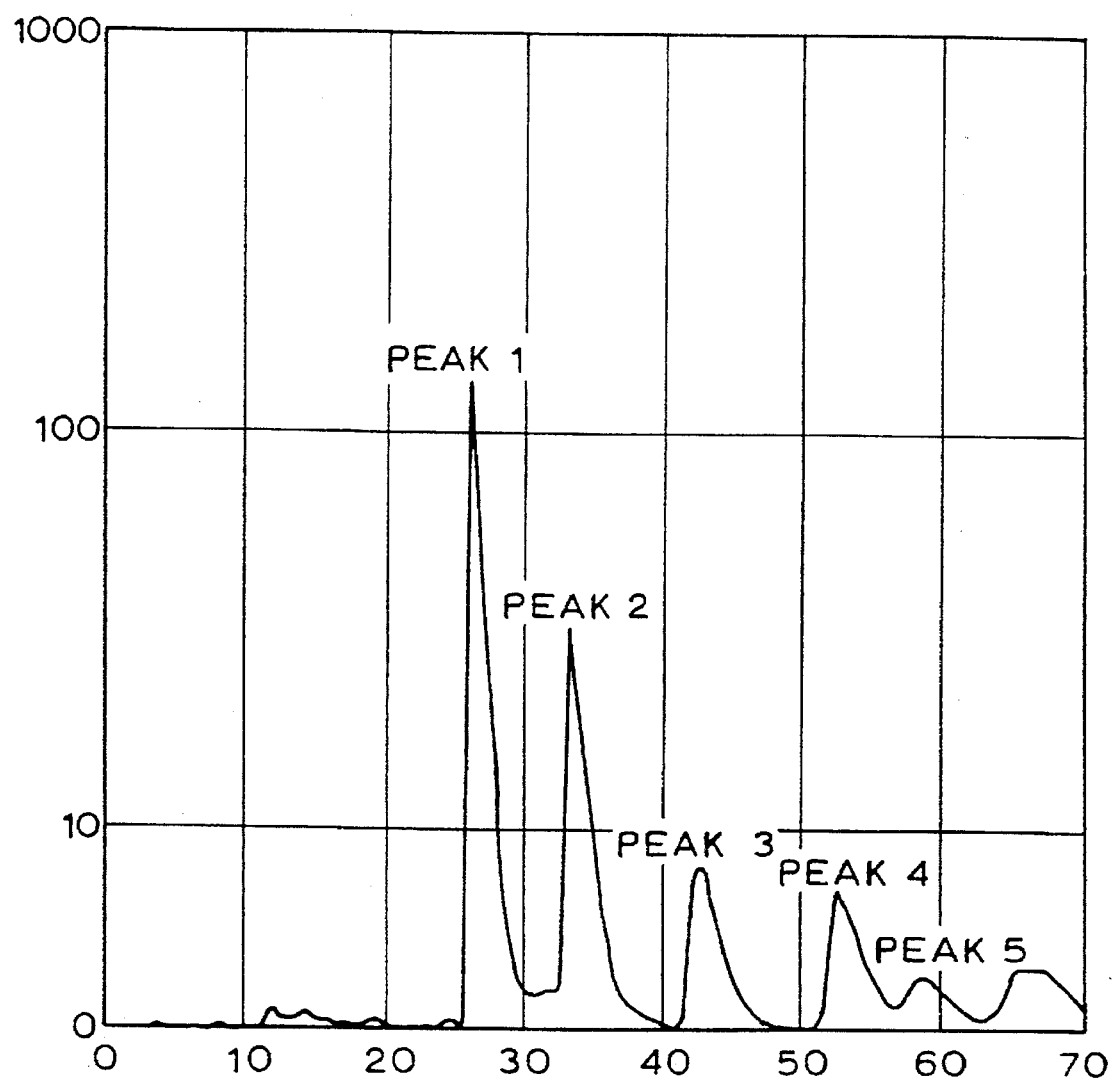
Figure 3:
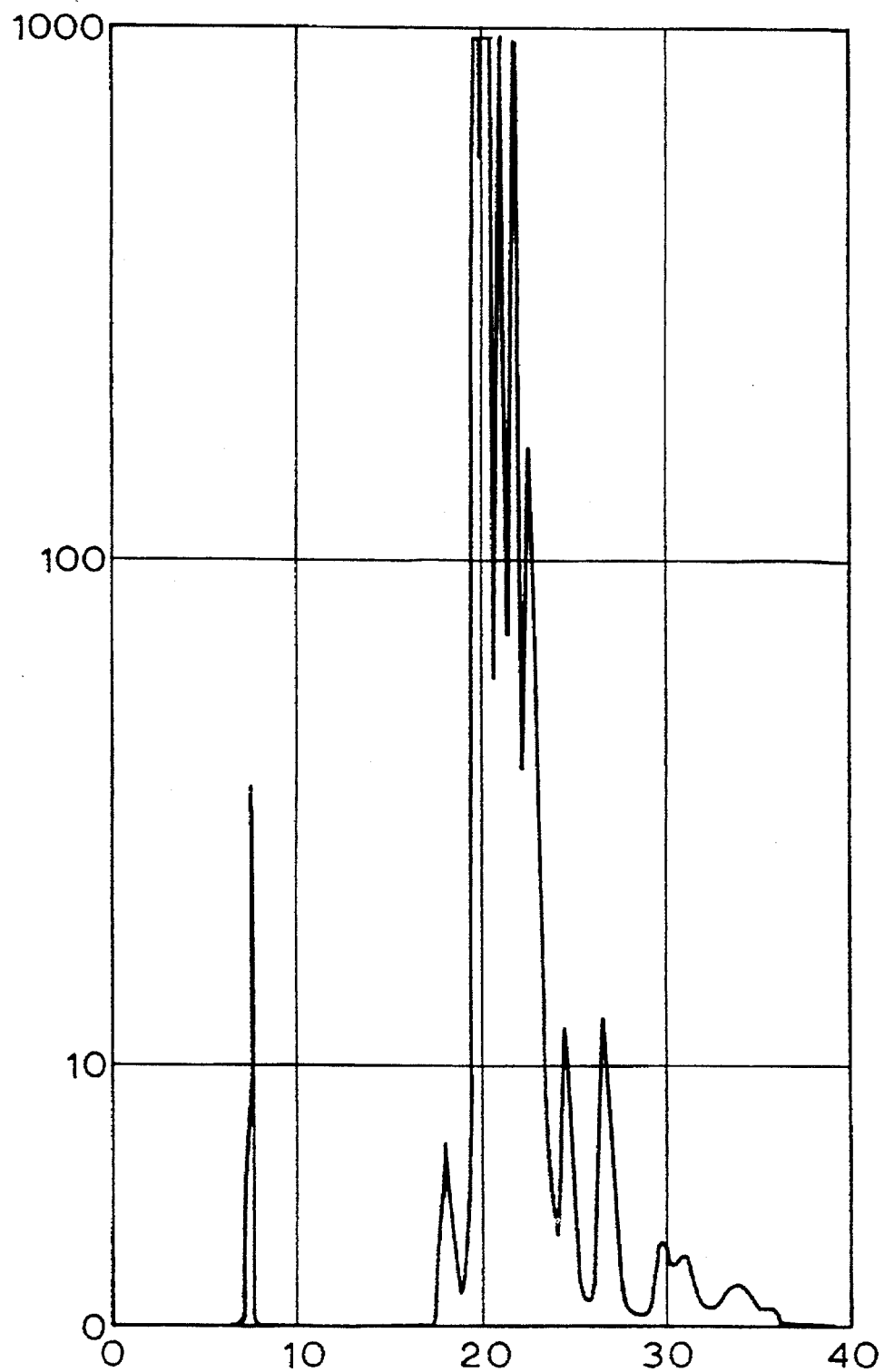
Figure 4:
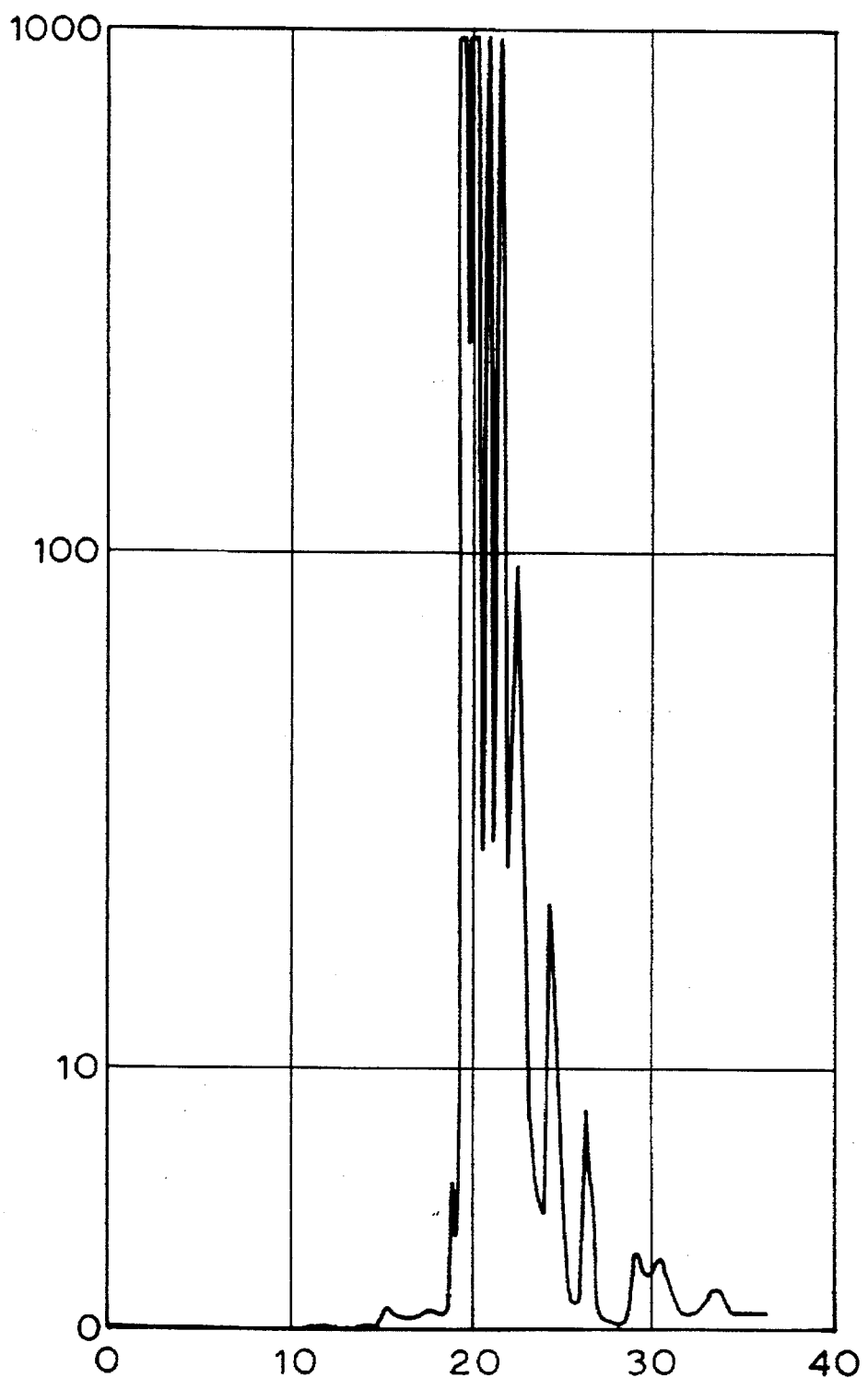

FIGS. 2–4 are profiles of the separation of the mixture of carboxylated Vitamin $B_{12}$ obtained in Runs 4, 2, and 3, respectively.

These results demonstrate that with a properly chosen solvent system and preparative HPLC column, the separation profile of the mixture of the carboxylated Vitamin $B_{12}$ can be adjusted. For example, as seen in FIG. 2 and FIG. 5A which show the profile of the analytical HPLC of the same mixture of carboxylated Vitamin $B_{12}$ (See D below), Peak 3 of FIG. 5A (retention time of 13.84 min.) was split into peaks 3 and 4 (FIG. 2) using the preparative column.

D. Analytical HPLC Profile of the Carboxylated Vitamin $B_{12}$ Derivatives 5 to 20 ug of the mixtures of carboxylated Vitamin $B_{12}$ prepared in A, B, and Run 2 of C, in 20 ul of water were each injected into a Beckman 344 HPLC system (Beckman Instruments, San Ramon, Calif.). The HPLC system contained a 3.9 mm×30 cm stainless steel column packed with uBondapak C18 10 um particles with irregular shape and 120A pore size (Waters Associates, Milford, Mass.). The mixtures were each eluted isocraticly from the column using 10% acetonitrile and 90% 0.05M triethylammonium acetate, pH4.5. The flow rate of the elution was 1.5 ml/min. and the eluted materials were detected at a wavelength of 280 nm.

Figure 5A:
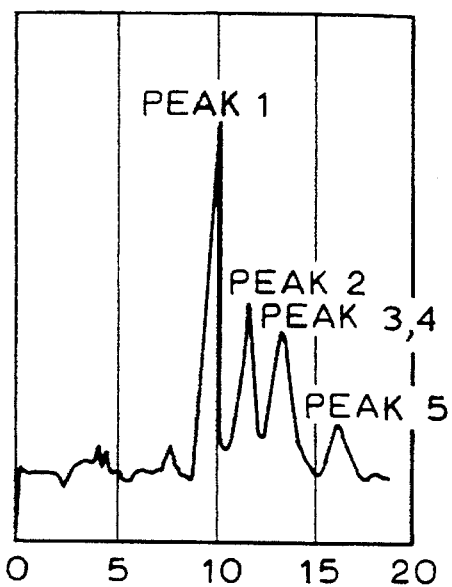
Figure 5B:
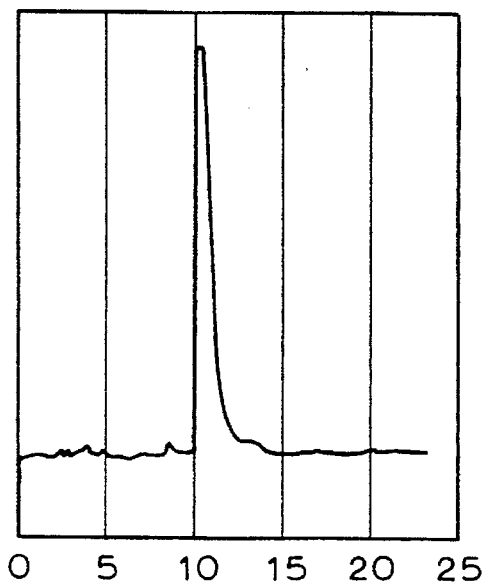
Figure 5C:
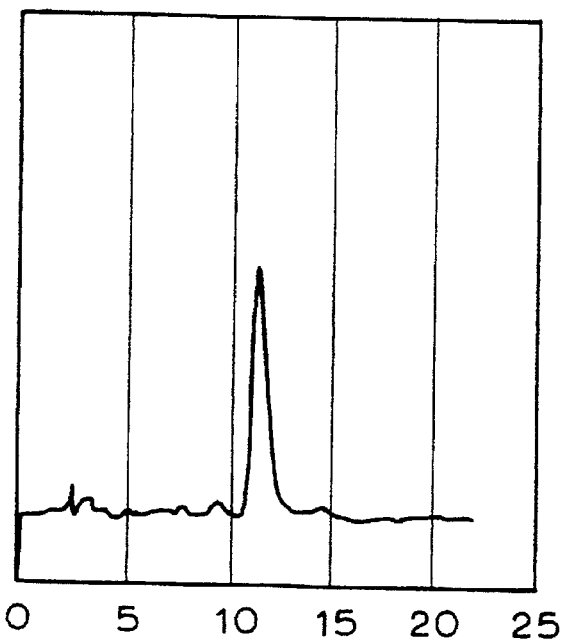

FIG. 5A is a profile of the separation of the carboxylated Vitamin $B_{12}$ from A. Peak 1 represents the unreacted Vitamin $B_{12}$, Peak 2 (retention time of 11.97 min.) and peak 3 (retention time of 13.84 min.) represent the 3 incompletely separated monocarboxylated Vitamin $B_{12}$ forms present in the mixture. Peak 5 in FIG. 5A probably represents the dicarboxylated Vitamin $B_{12}$ form.

Figure 5D:
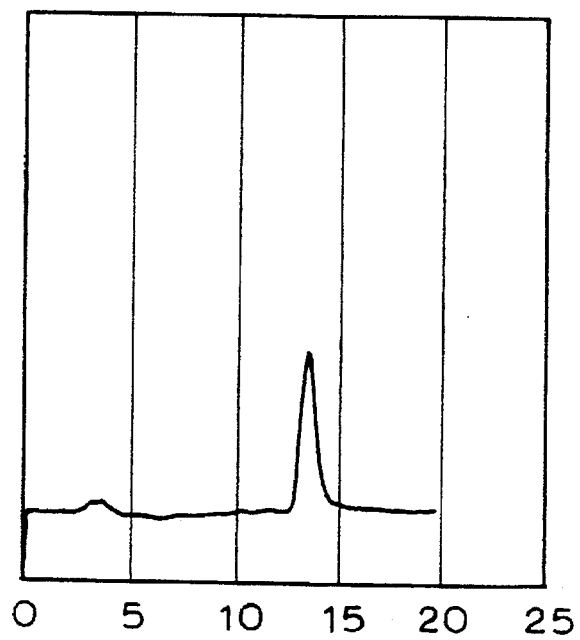
Figure 5E:
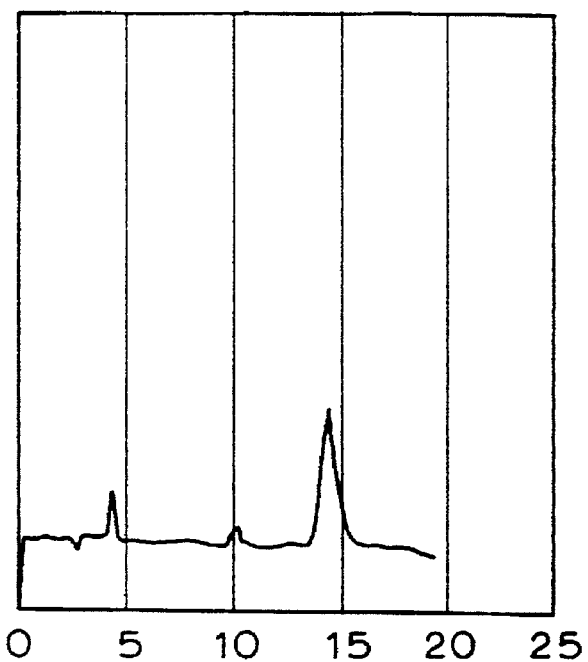
Figure 5F:
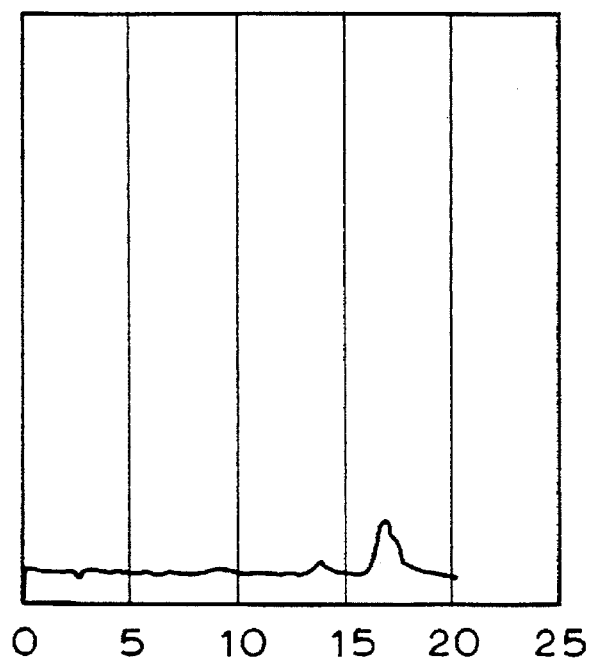

FIGS. 5B–5F are the analytical HPLC profiles of the separated peaks 1–5 (FIG. 2) obtained in Run 2 of C. FIG. 5D and FIG. 5E show the close retention times (13.54 min. and 14.33 min., respectively) of the two different monocarboxylated Vitamin $B_{12}$ forms which comprised peak 3 of FIG. 5A and peaks 3 and 4 of FIG. 2.

Figure 6:
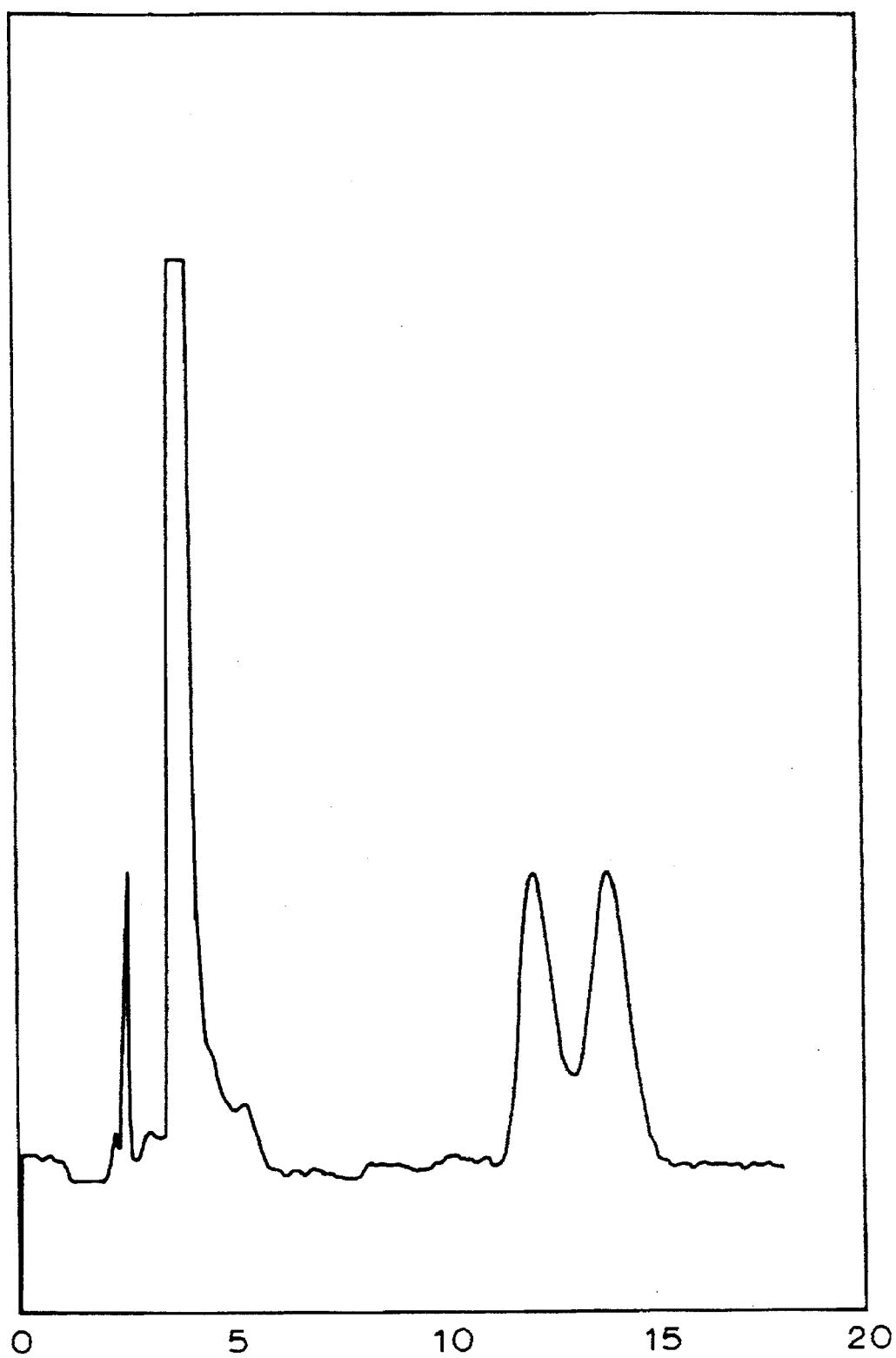

FIG. 6 is the analytical HPLC profile of the mixture of the 3 monocarboxylated Vitamin $B_{12}$ forms from B. Peaks 12.22 min. and 13.9 min. of FIG. 6 have nearly the same retention times as Peaks 2 and 3 of FIG. 5A.

EXAMPLE 6

Preparation of Conjugates from Monocarboxylic Vitamin $B_{12}$ and DMAE-ED ($B_{12}$-ED-DMAE)

Using the 3 monocarboxylic Vitamin $B_{12}$ forms prepared and isolated in Example 5 (designated hereinafter as monocarboxylic Vitamin $B_{12}$ forms I, II, and III, which have retention times of 11.58, 13.54, and 14.33 min., respectively) and DMAE-ED prepared in Example 1, three separate but similar conjugating reactions were carried out to prepare the tracers as following:

A solution of monocarboxylic Vitamin $B_{12}$ form I (10 mg., 7.4 umole) in 1.8 ml of DMF was cooled in ice bath, treated with triethylamine (10.5 ul, 74 umole, in 100 ul DMF) and ethyl chloroformate (2.8 ul, 30 umole, in 100 ul DMF) to form a reaction mixture. After stirring for 30 minutes, the reaction mixture was evaporated to dryness to remove the excess ethyl chloroformate to produce a residue. DMAE-ED (3.4 mg, 6.7 umole) and triethylamine (5.2 ul, 37 umole) in 2 ml of DMF, were added to the residue to form a second reaction mixture. The second reaction mixture was stirred at room temperature overnight and then evaporated to dryness under vacuo. The crude products so obtained were purified on one analytical silica gel 20×20 cm TLC plate (Silica gel 60, Merck & Co, Inc.), developed with chloroform/methanol/water (55:40:5).

Two red bands (hereinafter referred to as the upper and the lower bands) which developed between Rf of 0.47–0.57 were each separately stripped and eluted with the same solvent system. Each eluent was evaporated to dryness to produce a $B_{12}$-ED-DMAE tracer.

The same procedure described above was repeated for monocarboxylic Vitamin $B_{12}$ forms II and III. As a result, from the 3 monocarboxylic Vitamin $B_{12}$ forms, a total of six $B_{12}$-ED-DMAE conjugates (designated 1 through 6) were isolated. Conjugates 1 and 2 were prepared from form I, 3 and 4 were prepared from form II, and 5 and 6 were prepared from form III. The conjugates were each diluted in phosphate buffered saline (PBS) with 0.1% bovine serum albumin (BSA) and were simultaneously screened for tracer activity (FIG. 7) using the following procedure:

A series of Vitamin $B_{12}$ standards in 1% human serum albumin (HSA) (in 120 mM PBS containing 0.2% sodium azide and 0.4 g/l merthiolate) were treated by adding 1/20 volume of 1.35M DTT, to produce treated standards. 100 ul of each treated standard was added to a 12×75 mm plastic tube. To each tube was then added 100 ul of 0.5N NaOH and 0.5 ml of an IF-PMP (100 ug) (prepared as described in Example 12A below except that the suspension contained 3 ug IF/g PMP, the heat stress step was omitted, and the IF-PMP was resuspended in 0.16M boric acid, 10 mM phosphate, 0.127M NaCl, and 0.1% sodium azide, pH 7.0). 100 ul of PBS/BSA containing 12–29×10$^6$ relative light units (RLU) (1 RLU=1 photon count) of the $B_{12}$-ED-DMAE conjugate to be tested, was added to each tube and the tubes were then incubated at room temperature for one hour. The solid phase in each tube was magnetically separated from the supernatant and the supernatant was then decanted. The solid phase in each tube was washed once with 1 ml of water. The solid phase was then resuspended in 100 ul water and counted as described in Example 12B below. Table 1 shows the results obtained. In Table 1 T represents the total RLU of each conjugate added, $B_o$ represents the total RLU associated with the solid phase in the final resuspension, for each conjugate, in the absence of any Vitamin $B_{12}$, and $B_o/T$ is the percentage of the total RLU added which were associated with the solid phase, for each conjugate.

TABLE 1

| Conjugate | T | $B_o$ | $B_o/T$ % |
|---|---|---|---|
| 1 | $18 \times 10^6$ | $3.8 \times 10^4$ | 0.21 |
| 2 | $29 \times 10^6$ | $5 \times 10^4$ | 0.17 |
| 3 | $17.5 \times 10^6$ | $7.7 \times 10^4$ | 0.44 |
| 4 | $15.2 \times 10^6$ | $6.6 \times 10^4$ | 0.44 |
| 5 | $20.6 \times 10^6$ | $26.1 \times 10^4$ | 1.27 |
| 6 | $12 \times 10^6$ | $20 \times 10^4$ | 1.67 |

Figure 7:
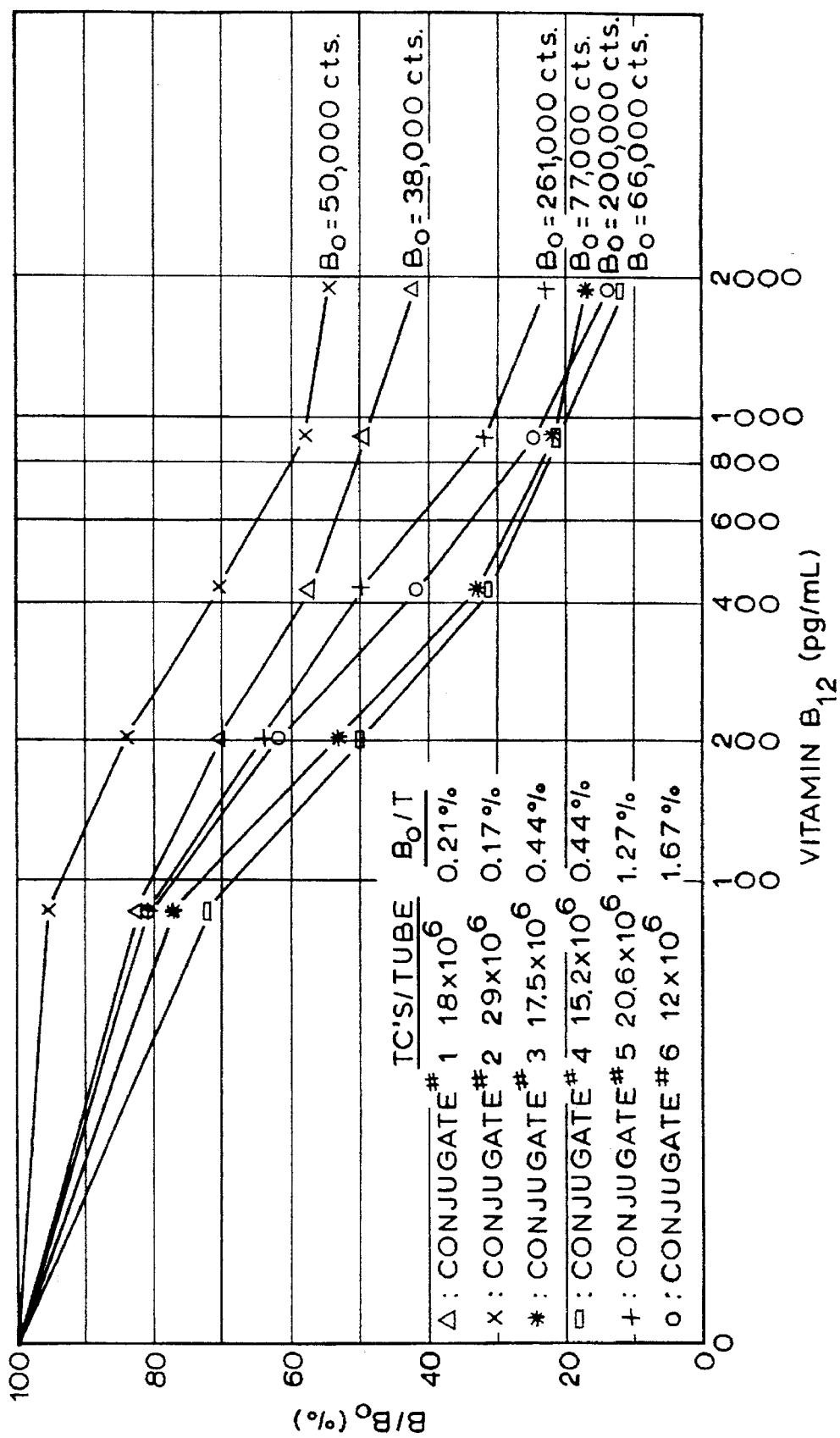

FIG. 7 is a plot of $B/B_o$ against Vitamin $B_{12}$ concentration for each of the conjugates. B represents the total RLU associated with the solid phase in the final resuspension for a particular concentration of Vitamin $B_{12}$ in the sample and $B_o$ is as described above. The conjugate that performed the best (highest $B_o/T$ value) came from the lower band (conjugate #6) which originated from monocarboxylic Vitamin $B_{12}$ III.

100 ug of the $B_{12}$-ED-DMAE conjugate #6 was separated on an analytical HPLC system as described in Example 5D eluted with mixture of 0.05M triethylammonium acetate, pH 4.5 (Solvent A) and acetonitrile (Solvent B) in linear gradient from 40% B/60% A to 50% B/50% A over a 10 min. period. The flow rate of the eluent was 1 ml/min. and the eluted materials were detected at 260 nm. The chromatogram revealed the presence of two peaks (retention times of 5.66 min. and 7.86 min.). These two peaks when isolated and evaluated separately gave identical assay performance whether combined or alone.

EXAMPLE 7

Preparation of N-Trifluoroacetyl-Folic Acid (TFA-Fol)

A mixture of folic acid (1.0 g, 2.27 mmole) and trifluoroacetic anhydride (2 ml, 6.4 mmole) was stirred at room temperature for 1 hour and then evaporated under vacuo. The residue from the evaporation was triturated with a minimal amount of methanol and the supernatant removed by filtration. The resultant wet cake was evaporated to dryness to produce TFA-Fol with an Rf of 0.35 when chromotographed on a TLC plate (Silica gel 60, Merck & Co.) using chloroform/methanol/water (55:40:5).

EXAMPLE 8

Preparation of Folate-SulfoCys-ED-DMAE conjugate

A solution of TFA-Fol (27 mg, 0.05 mmole) (Example 7) in 3.75 ml of DMF was diluted with 1.8 ml of chloroform, cooled in an ice bath and treated with triethylamine (0.065 ml, 0.45 mmole) and ethyl chloroformate (0.03 ml, 0.3 mmole) to form a reaction mixture. After 30 min. of stirring, the reaction mixture was evaporated to dryness under vacuo. To the residue which resulted from the evaporation were added 4.5 ml of DMF/chloroform (2:1), SulfoCys-ED-DMAE (31 mg, 0.04 mmole) and triethylamine (0.035 ml, 0.24 mmole) to form a second reaction mixture. The second reaction mixture was stirred at room temperature overnight and evaporated to form a second residue.

The second residue was purified on a 10×20 cm silica gel preparative TLC plate (Silica gel 60, Merck & Co.) developed with chloroform/methanol/water (55:40:5).

The yellow band which developed at about an Rf of 0.64 was stripped and eluted with the same solvent system. The eluent was evaporated to produce crude TFA-Fol-SulfoCys-ED-DMAE (11 mg). TLC analysis of the product showed two major UV positive spots (Rf of 0.6 and 0.5). The spot having Rf of 0.5 was not affected by the subsequent deblocking conditions and was, therefore, considered as an undesirable contaminant.

The crude TFA-Fol-SulfoCys-ED-DMAE obtained above was treated with 200 ul of 36% HBr/Acetic acid at room temperature overnight to form a third reaction mixture. This third reaction mixture was treated with about 10 ml of anhydrous ethylether to form a precipitate. After 1 hour of standing, the supernatant was removed from the precipitate by careful pipeting. The precipitate was then dissolved in about 0.5 ml of chloroform/methanol/water (65:25:4) and purified on one 20×20 cm silica gel analytical TLC plate (Silica gel 60, Merck & Co., Inc.). The TLC plate was developed with chloroform/methanol/water (55:40:5). The yellow band which developed at Rf of 0.38 was stripped and eluted with the same developing solvent system. The eluent was evaporated to produce the Folate-SulfoCys-ED-DMAE conjugate.

EXAMPLE 9

Preparation of Cortisol-3-CMO-ED-DMAE Conjugate

A solution of 3-carboxylmethyloxime-cortisol (Cortisol-3-CMO, 10 mg, 0.022 mmole) (Steraloids, Wilton, N.H.) in 0.2 ml of DMF was diluted with 0.8 ml of chloroform, cooled in an ice bath, and treated with dicyclohexylcarbodiimide (DCC, 5.5 mg, 0.0266 mmole) in 0.2 ml of chloroform to produce a reaction mixture. After 10 min. of stirring, the reaction mixture was treated with a solution of DMAE-ED (5.5 mg, 0.01 mmole) in 0.4 ml of DMF to produce a second reaction mixture. The second reaction mixture was stirred at room temperature overnight and evaporated under vacuo. The residue from the evaporation was purified on a 10×20 cm silica gel preparative TLC plate (Merck & Co.) and developed with 10% methanol/chloroform. The yellow band which developed at Rf of 0.28 was stripped and eluted with 20% methanol/chloroform. The eluent was evaporated to give Cortisol-3-CMO-ED-DMAE (3.56 mg, 42%). FAB Mass Spectral analysis (performed by Institute of Chemical Analysis, Northeastern Univ., Boston, Mass.) in the positive ion mode gave a M+ peak of 845.

EXAMPLE 10

Preparation of Estradiol-6-CMO-ED-DMAE Conjugate

A solution of 6-carboxymethyloxime-17-beta-estradiol (Estradiol-6-CMO) (23.1 mg, 0.062 mmole) (Steraloids, Wilton, N.H.) in 2 ml of DMF/$CHCl_3$ (1:1) was cooled in an ice bath, and treated with DCC (15.4 mg, 0.074 mmole) to produce a reaction mixture. After 10 min. of stirring, the reaction mixture was treated with DMAE-ED (30.1 mg, 0.059 mmole) to produce a second reaction mixture. The second reaction mixture was stirred at room temperature overnight and evaporated under vacuo. The residue from the evaporation was purified on one 20×20 cm silica gel preparative TLC plate developed with 5% methanol/chloroform. The yellow band which developed at Rf of 0.17 was stripped and eluted with 20% methanol/chloroform. The eluent was evaporated to give Estradiol-6-CMO-ED-DMAE (11.9 mg, 26%). FAB Mass Spectral analysis (performed by Institute of Chemical Analysis, Northeastern University, Boston, Mass.) in the positive ion mode gave a M+ peak of 789.

EXAMPLE 11

Preparation of Thromboxane $B_2$-ED-DMAE Conjugate ($TxB_2$-ED-DMAE)

A solution of Thromboxane $B_2$ (TxB2) (2.5 mg, 0.0067 mmole) (Biomol, Plymouth Meeting, Pa.) in 0.4 ml of DMF/CHCl₃ (1:1) was cooled in an ice bath, treated with triethylamine (6 ul, 0.04 mmole), and ethyl chloroformate (2 ul, 0.02 mmole) to produce a reaction mixture. After 30 min. of stirring, the reaction mixture was evaporated to dryness. The residue from the evaporation was dissolved in 0.4 ml of DMF/CHCl₃ (1:1), treated with triethylamine (6 ul, 0.04 mmole) and DMAE-ED (4.5 mg, 0.009 mmole) to produce a second reaction mixture. The second reaction mixture was stirred at room temperature and evaporated under vacuo to form a second residue. The second residue was taken up in about 0.5 ml of chloroform/methanol/water (65:25:4) and purified on a 20×20 cm silica gel analytical TLC plate (Merck & Co.) developed with 15% methanol/chloroform.

The major yellow band which developed at Rf of 0.49 was stripped and eluted with 15% methanol/chloroform. The eluent was evaporated to produce $TxB_2$-ED-DMAE.

EXAMPLE 12

Vitamin $B_{12}$ Assay

A. Preparation of Intrinsic Factor Paramagnetic Particles (IF-PMP)

PMP (obtained from Advanced Magnetics Inc., Cambridge, Mass.) were activated with glutaraldehyde as described in U.S. Pat. No. 4,454,083.

To a solution of human serum albumin (HSA) (400 mg, Immunosearch, Toms River, N.J.) in 25 ml of 10 mM sodium phosphate, pH 7.4, was added purified hog Intrinsic Factor (purchased from Dr. R. H. Allen, University of Colorado Medical Center, Denver, Colo.) (75 ug) in 5 ml of saline to produce a protein mixture.

The protein mixture was added to a suspension of the activated PMP (5 g) in 60 ml of 10 mM sodium phosphate and shaken at room temperature overnight to produce IF-PMP.

The IF-PMP were then washed and the excessive activated groups were quenched with glycine.

The IF-PMP were resuspended in 200 ml of 30 mM PBS with 0.1% sodium azide, 0.1% BSA and 0.001% BgG, cured at 50° C. for 16 hrs, washed three times with 10 mM sodium phosphate, washed three times with Glycine Buffer (0.325 glycine, 0.1% sodium azide, and 0.1% BSA, pH 7.8), resuspended in the Glycine Buffer (25 mg/ml) and stored at 4° C. until needed.

B. Simultaneous Assay

A series of standards in 6% HSA (in 120 mM PBS with 0.2% sodium azide and 0.4 g/l merthiolate) with known increasing amounts of Vitamin $B_{12}$, were added to 12×75 mm plastic tubes (100 ul/tube). 0.1 ml of Releasing Agent (0.5M NaOH, 50 ug/ml KCN, 0.3 ug/ml cobinamide, 0.064M dithiothreitol) was added to the tubes and the tubes were incubated at room temperature for 15 minutes. The IF-PMP prepared in A was diluted 1:312 in the Glycine Buffer (80 ug/ml). 0.5 ml of the diluted IF-PMP (40 ug/tube) and 0.1 ml of the $B_{12}$-ED-DMAE conjugate #6 prepared in Example 6, diluted in PBS with 0.1% BSA and 0.1% sodium azide (4×10⁶ RLU/tube), were then added to the tubes and the tubes were incubated for 60 min. at room temperature.

The tubes were then placed in a magnetic rack useful for magnetic separation of paramagnetic particles in tubes (available from Ciba Corning Diagnostics Corp., Medfield, Mass.). The magnetic field separated the particles from the supernatant and the supernatant was then decanted. The particles were washed once in 1 ml of water, vortexed, magnetically separated from the wash and decanted. The particles were then resuspended in 0.1 ml of a 1 mM ethyl maleimide.

Figure 8:
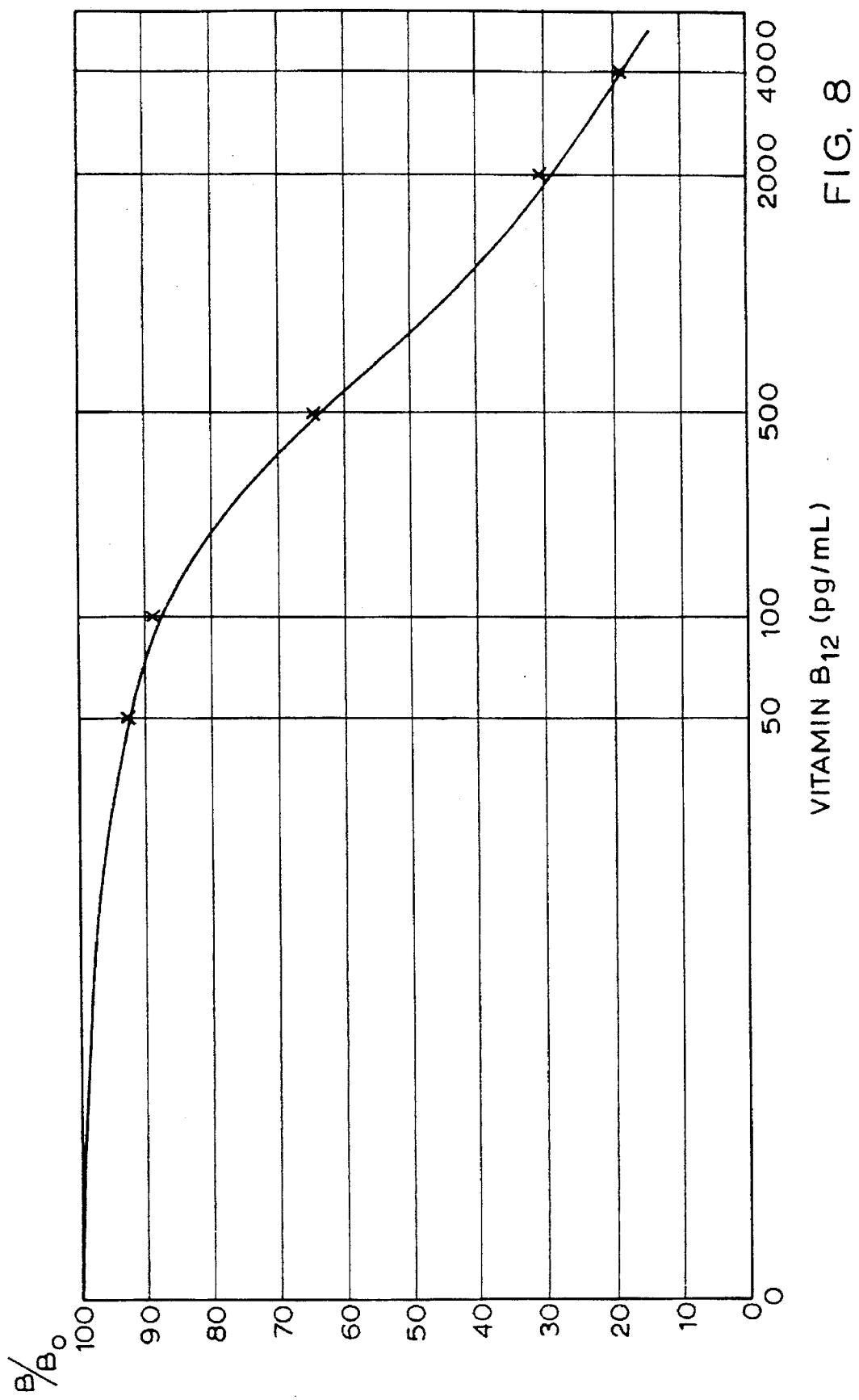

The tubes were then placed in a luminometer (MAGIC® LITE Analyzer, Ciba Corning Diagnostics Corp., Medfield, Mass.). 0.3 ml of a solution of 0.5% hydrogen peroxide in 0.1N HNO₃ was added to each tube by the luminometer and the light emission was triggered by the addition of 0.3 ml of 0.25N NaOH containing ARQUAD surfactant (Armack Chemicals, Chicago, Ill.). The measured RLU's of each tube normalized against the RLU's of the zero standard were plotted against their respective Vitamin $B_{12}$ concentrations as shown in FIG. 8.

C. Split Incubation Assay

Figure 9:
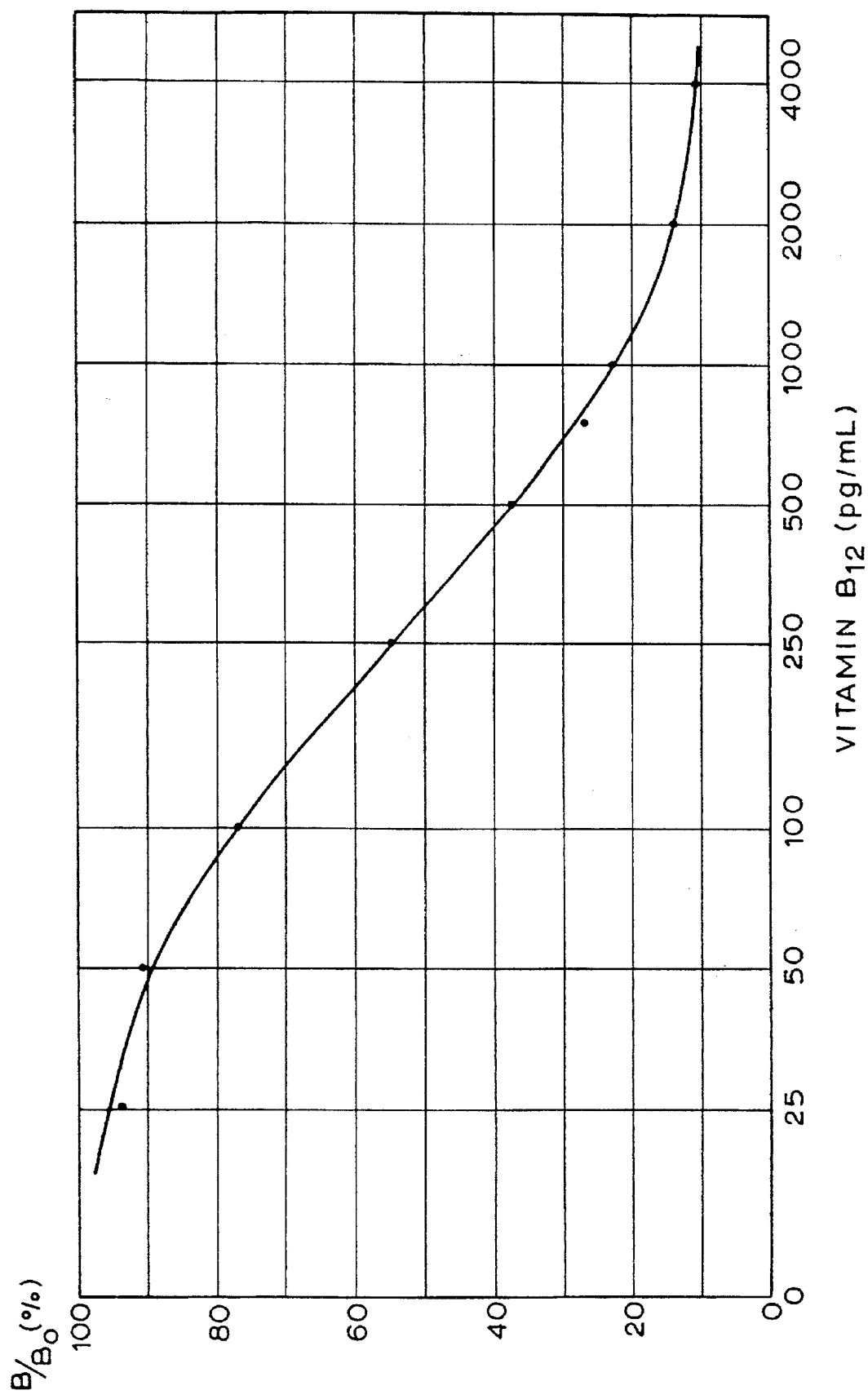

A series of Vitamin $B_{12}$ standards in 5% HSA (in PBS with 0.2% sodium azide, 2 mg/l amphotericin and 24 mg/l gentamycin) with known increasing amounts of Vitamin $B_{12}$ were added to tubes (100 ul/tube) and incubated with the Releasing Agent of B except that the cobinamide was omitted. 0.5 ml of the diluted IF-PMP of B (40 ug/tube), but with 0.06 ug/ml cobinamide added to the buffer, was added to each tube and the tubes were then incubated for 45 minutes at room temperature. 0.1 ml of the $B_{12}$-ED-DMAE conjugate #6 (8×10⁶ RLU) prepared in Example 6 diluted with 10 mM PBS, pH 7.4, containing 0.1% sodium azide and 0.1% BSA, was then added to each tube and the tubes were then incubated for 30 minutes at room temperature. The particles in the tubes were magnetically separated, washed, resuspended, and counted as described in B. The measured RLU's normalized against the RLU's of the zero standard for each tube were plotted against their respective Vitamin $B_{12}$ concentration as shown in FIG. 9.

EXAMPLE 13

Folate Assay

A. Reagents

The standards used in the Folate assay were PGA (pteroylglutamic acid) (Sigma Chemical Co, St. Louis, Mo.) dissolved in 120 mM PBS, pH 7.4 with 4% HSA, 0.2% sodium azide, 2 mg/l amphotericin, and 24 mg/l gentamycin added as preservatives. The folate concentrations were zero, 0.25, 0.5, 1.0, 2.5, 5, 10, 15, 20, and 30 ng PGA/ml.

The Releasing Agent was 0.5N NaOH containing 64 mM dithiothreitol.

Folate-SulfoCys-ED-DMAE conjugate (8.8×10¹¹ RLU) obtained in Example 8 was first dissolved in 22 ml of 10% DMF/water. The solution was then further diluted 1:11250 with 325 mM glycine containing 0.1% BSA and 0.1% sodium azide to form a second solution. This second solution was filtered through a 0.2 um cellulose acetate filter (Schleicher and Schuell, Keene, N.H.) to produce a tracer solution. 500 ul of the tracer solution was added per test.

The binder in the assay was Folate Binding Protein (FBP) (a bovine milk lactoglobulin, purchased from Dr. R. H. Allen, University of Colorado Medical Center, Denver, Colo.). FBP-PMP and Bovine Gamma Globulin (BgG)-PMP were prepared by the method described in U.S. Pat. No. 4,454,088. The FBP-PMP (0.96 mg/ml) was diluted 1:60 in 10 mM PBS with 0.1% BSA and 0.1% sodium azide, pH 7.4. This was bulked with BgG-PMP at 0.4 mg/ml to form the solid phase binder. 100 ul of this solid phase binder was added per test, resulting in the addition of 1.6 ug FBP-PMP and 40 ug BgG PMP. In the final assay there was 100 ul of sample or standard, 100 ul of Releasing Agent, 500 ul of tracer solution and 100 ul of solid phase binder, for a total assay volume of 800 ul.

B. Assay Procedure

Figure 10:
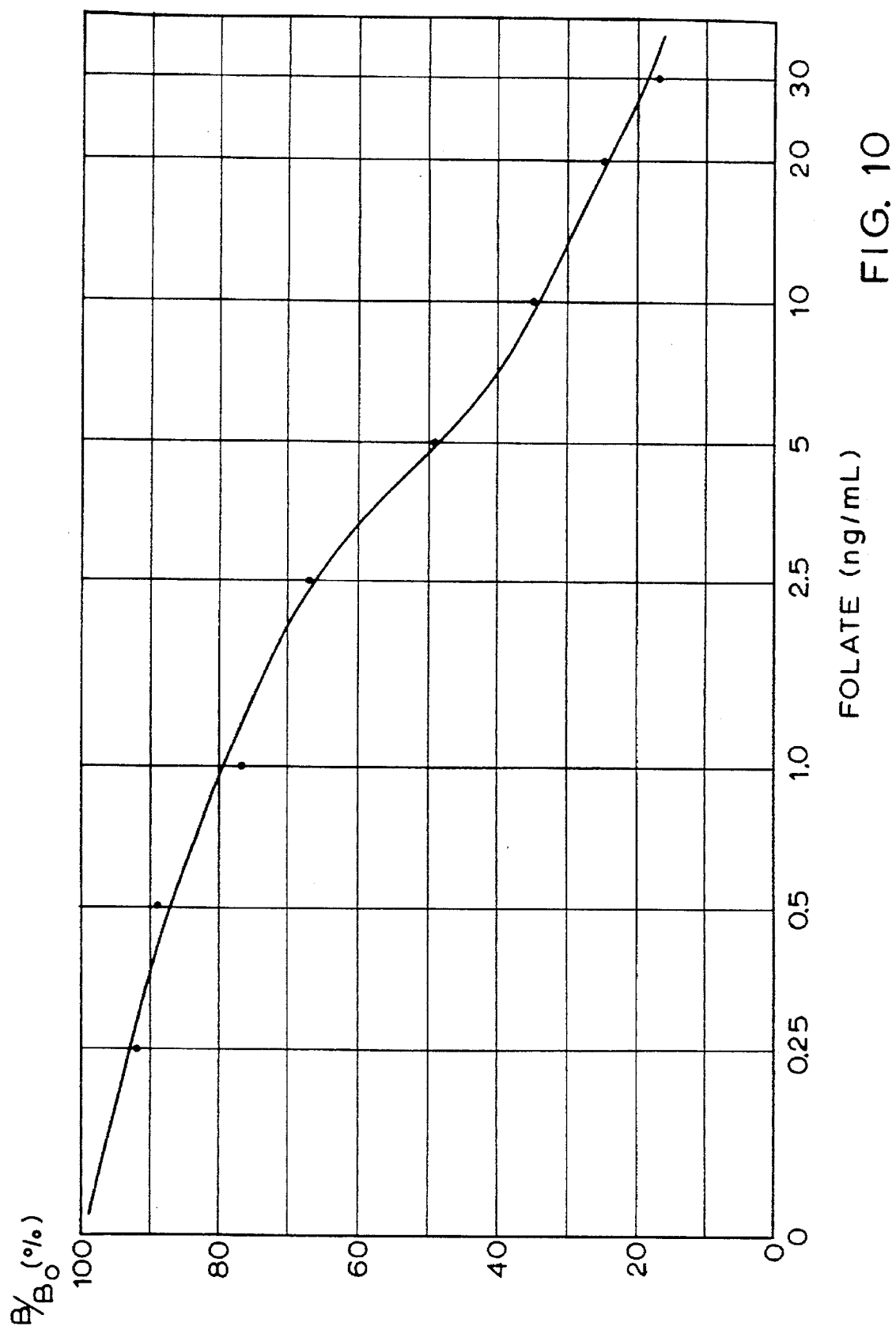

Standards or samples (100 ul) were added to 12×75 mm polystyrene tubes (Sarstedt, West Germany). To each tube was added 100 ul of the Releasing Agent of A. The tubes were vortexed and incubated for 15 min. at room temperature. The tracer solution of A (500 ul) was then added to each tube, followed by the addition of the solid phase binder of A (100 ul). The tubes were vortexed again and incubated for one hour at room temperature. The tubes were then put on a magnetic separator for 3 minutes, decanted, and blotted. 1 ml of deionized water was added to each tube to wash out excess unbound tracer. The solid phase in the tubes was magnetically separated for 3 min., the supernatant decanted, and the tubes drained for 3 minutes. To the resulting pellets in the tubes was added 100 ul of 1 mM ethyl maleimide. The tubes were then placed in a luminometer and counted as described in Example 12B. The RLU's for each standard were normalized against the RLU's of the zero standard and plotted against the respective folate concentration of the standards to give a displacement curve as shown in FIG. 10.

EXAMPLE 14

Cortisol Assay

A. Reagent Preparation

The Cortisol-ED-DMAE conjugate of Example 9 was dissolved in methanol and kept at −20° C. as a stock solution. The final cortisol-ED-DMAE conjugate was diluted in a buffer containing 10 mM sodium phosphate, pH 7.4, 0.1% bovine serum albumin, 0.4 mg/ml of 8-anilino-1-naphthalenesulphonate, 0.1% Triton X-100, and 0.05% sodium azide, to produce the tracer solution.

Rabbit anti-cortisol antiserum was bought from Bioclinical Group, Cambridge, Mass. The antibody was immobilized on PMP (Advanced Magnetics Inc.) as described in U.S. Pat. No. 4,554,088 except that 0.01M sodium acetate buffer, pH 5.5, was used instead of 0.1M sodium phosphate buffer, pH 7.4. The final PMP wet cake was diluted with a buffer containing 0.01M sodium phosphate, 0.1% bovine serum albumin, 4 ng/ml 11-deoxycortisol, and 0.4 mg/ml 8-anilino-1-naphthalene sulfonate, pH 7.4, to form a PMP suspension (10 mg/ml).

Figure 11:
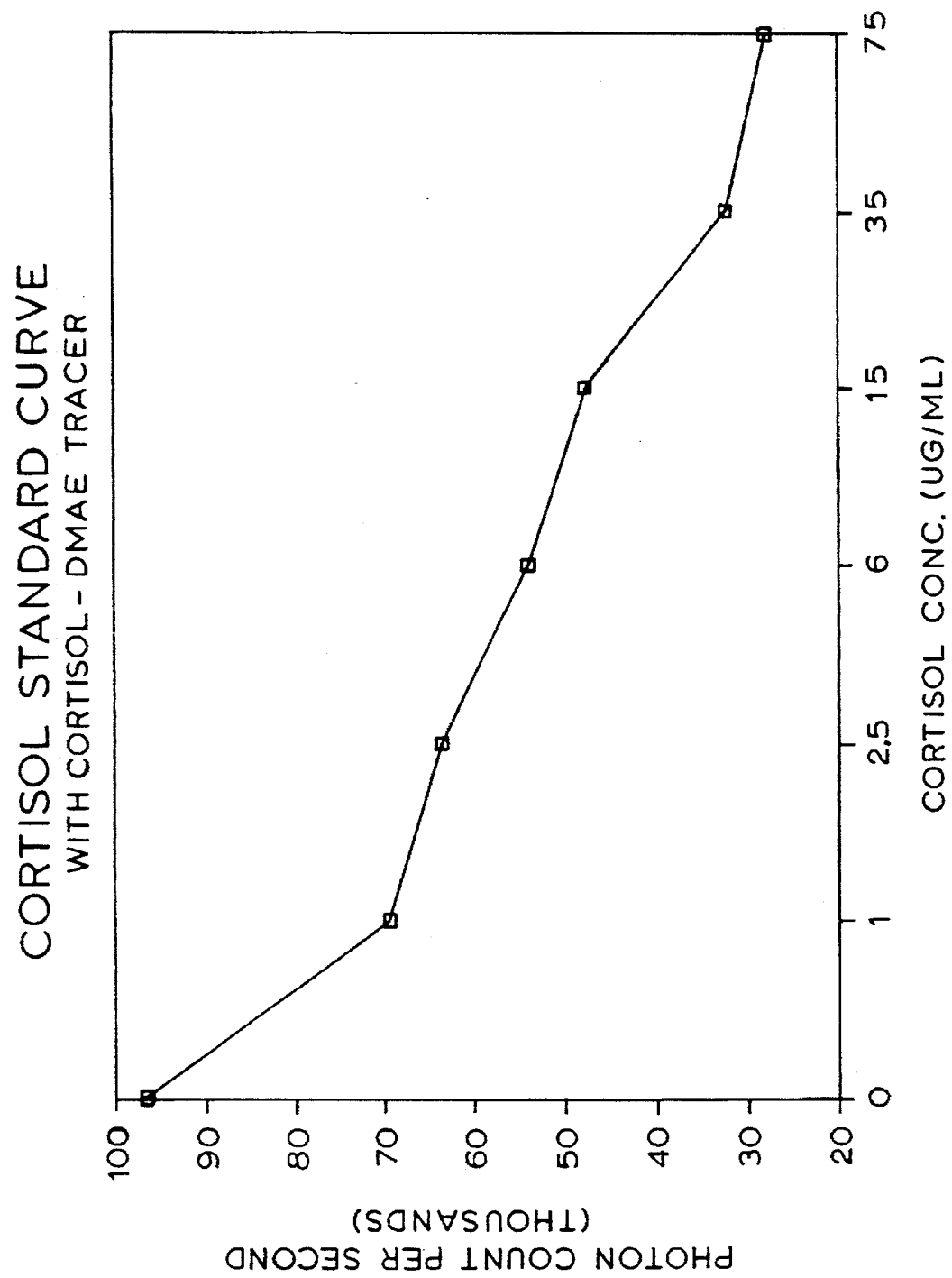

B. Assay Procedure 25 ml each of cortisol standards with concentrations from 0 to 750 ng/ml were added to 12×75 mm polystyrene test tubes (Sarstedt, West Germany) in duplicate. 100 ul of the tracer solution of A with total activity of $10^6$ RLU were then added to the tubes followed by 500 ul of the diluted PMP suspension of A. After vortexing, the tubes were incubated for 1 hour at room temperature. The PMP in the tubes were magnetically separated from the supernatant. The supernatant in each tube was then decanted and the PMP in each tube were washed once with 500 ul of 0.87% saline and then resuspended in 100 ul of water. The tubes were then placed in a luminometer and counted as described in Example 12B. A standard curve in FIG. 11 shows the displacement of tracer bound to PMP by added cortisol in the standard. The displacement is inversely proportional to the concentration of the cortisol in the standard.

EXAMPLE 15

Estradiol Assay

A. Reagent Preparation

The Estradiol-ED-DMAE conjugate of Example 10 was dissolved in methanol and kept at −20° C. as a stock solution. The stock solution was diluted with 0.01M sodium phosphate buffer, pH 7.4, containing 0.1% bovine serum albumin, 0.15M NaCl, and 0.05% sodium azide to form a tracer solution.

Monoclonal anti-estradiol antibody was produced in mice (A/J) by immunization with a BSA-estradiol conjugate and subsequent fusion of the splenocytes with Sp2/0-Ag14 myeloma cells by the procedure described by Kohler and Milstein in Nature (London), vol. 256, pp. 495–497 (1975). Hybridoma cells secreting anti-estradiol antibody were detected by the following procedure: Supernatant from the cells were diluted 1:5 in phosphate buffered saline containing 1 mg/ml bovine serum albumin. 100 ul of each diluted supernatant and 100 ul of acridinium ester-labelled estradiol-fowl gamma globulin as tracer were added to a test tube and incubated for one hour at room temperature. Goat anti-mouse IgG coupled to paramagnetic particles were added to each tube and incubated further for 10 minutes at room temperature. The particles were magnetically separated and read on a luminometer for tracer bound to the particles. The cells that tested positive (i.e., produce photon counts over background) were plated at 0.1 cell/well and retested after growth.

Cells resulting from this regrowth which tested positive were then injected intraperitoneally into pristane-primed mice ($CAF_1$). Ascitic fluid from these mice was collected after 3–5 weeks. The anti-estradiol antibody was used directly without further purification.

Goat anti-mouse IgG PMP particles were prepared by immobilizing the IgG fraction of goat anti-mouse IgG antiserum (Jackson Laboratory, Pa.) on paramagnetic particles by the method described in U.S. Pat. No. 4,454,088. The final PMP wet cake was diluted with phosphate buffered saline containing 1 mg/ml bovine serum albumin (PBS/BSA) to produce a PMP suspension with a final concentration of 10 mg/ml.

Figure 12:
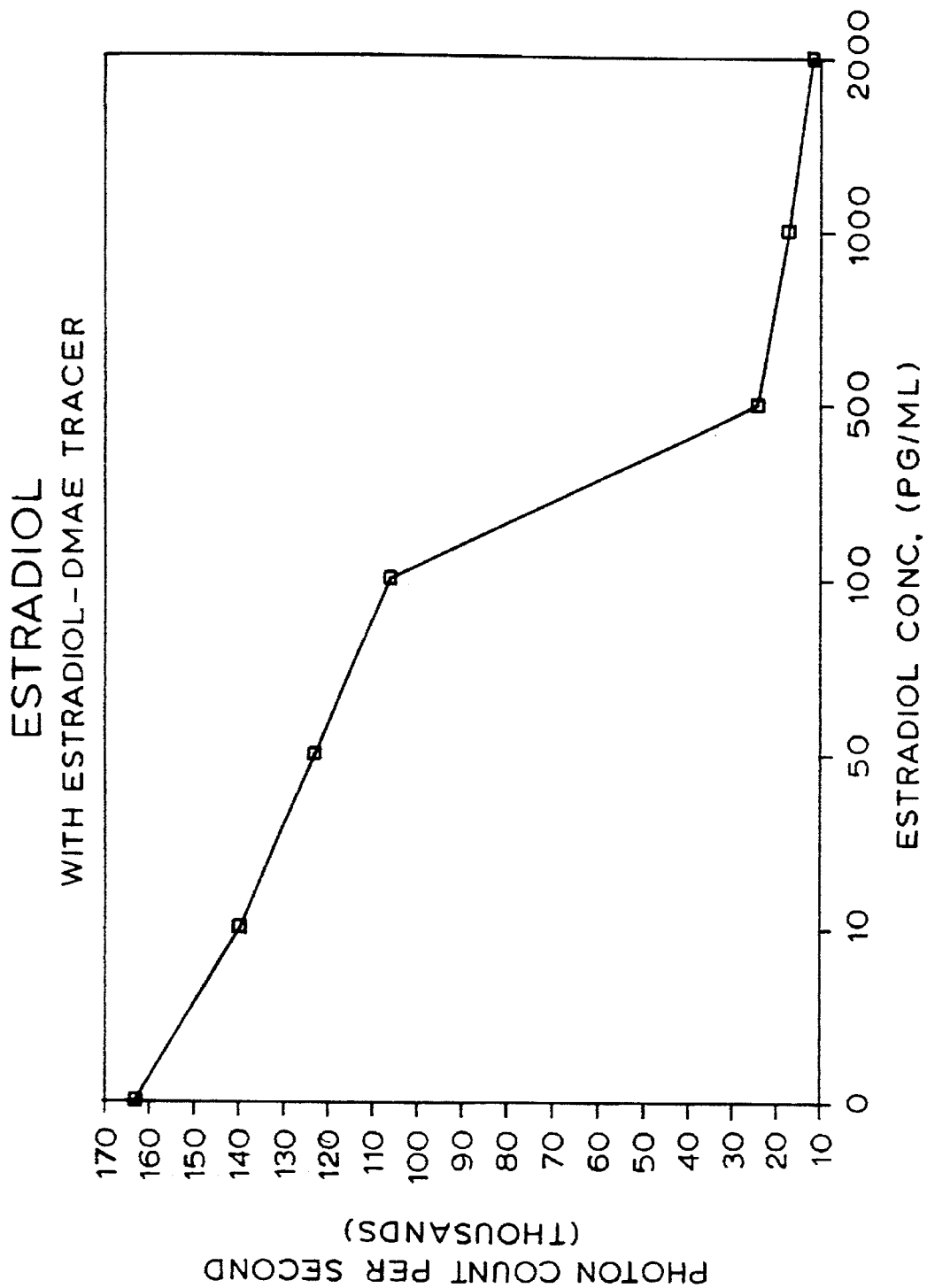

B. Assay Procedure 50 ul each of a series of estradiol standards with concentration range from 0 to 2000 pg/ml were added to 12×75 mm polystyrene test tubes (Sarstedt, West Germany) followed by the addition of 100 ul of the tracer solution of A with total activity of 385,000 RLU. 100 ul of the ascitic fluid from A was diluted 1:20000 in PBS/BSA buffer and then was added to each tube. The tubes were all vortexed and incubated for one hour at room temperature. The PMP suspension of A was diluted in PBS/BSA to a final concentration of 80 ug/ml. 500 ul of the diluted PMP suspension was then added to each of the test tubes. The tubes were then vortexed and incubated for 30 minutes at room temperature. The PMP in the tubes were then magnetically separated. The PMP in each tube was then washed once with 500 ul of saline containing 0.05% Triton X-100, magnetically separated, and the supernatant decanted. The PMP was then resuspended in 100 ul of water. The tubes were then placed in a luminometer and counted as described in Example 12B. The displacement curve in FIG. 12 shows that the photon counts are inversely proportional to the concentration of estradiol in the standards.

EXAMPLE 16

Thromboxane $B_2$ ($TxB_2$) assay

A. Reagent preparation

The $TxB_2$-ED-DMAE conjugate of Example 11 was dissolved in methanol and kept at −80° C. as a stock solution. The stock solution was diluted with 0.01M sodium phosphate buffer, pH 7.4, containing 0.1% BSA, 0.15M NaCL and 0.05% sodium azide to produce the tracer solution.

Rabbit anti-$TxB_2$ antiserum was bought from Cayman Chemicals Co., Ann Arbor, Mich.. The antiserum was diluted with 0.01M sodium phosphate buffer, pH 7.4, containing 0.15M sodium chloride, 1 mg/ml bovine serum albumin, 0.05% sodium azide.

Goat anti-rabbit IgG PMP was prepared by immobilizing the IgG fraction of goat anti-rabbit IgG antiserum (Jackson Laboratory, Pa.) on paramagnetic particles (PMP) by the method described in U.S. Pat. No. 4,454,088. The final PMP wet cake was diluted with PBS/BSA buffer (10 mg/ml) to produce a PMP suspension.

Figure 13:
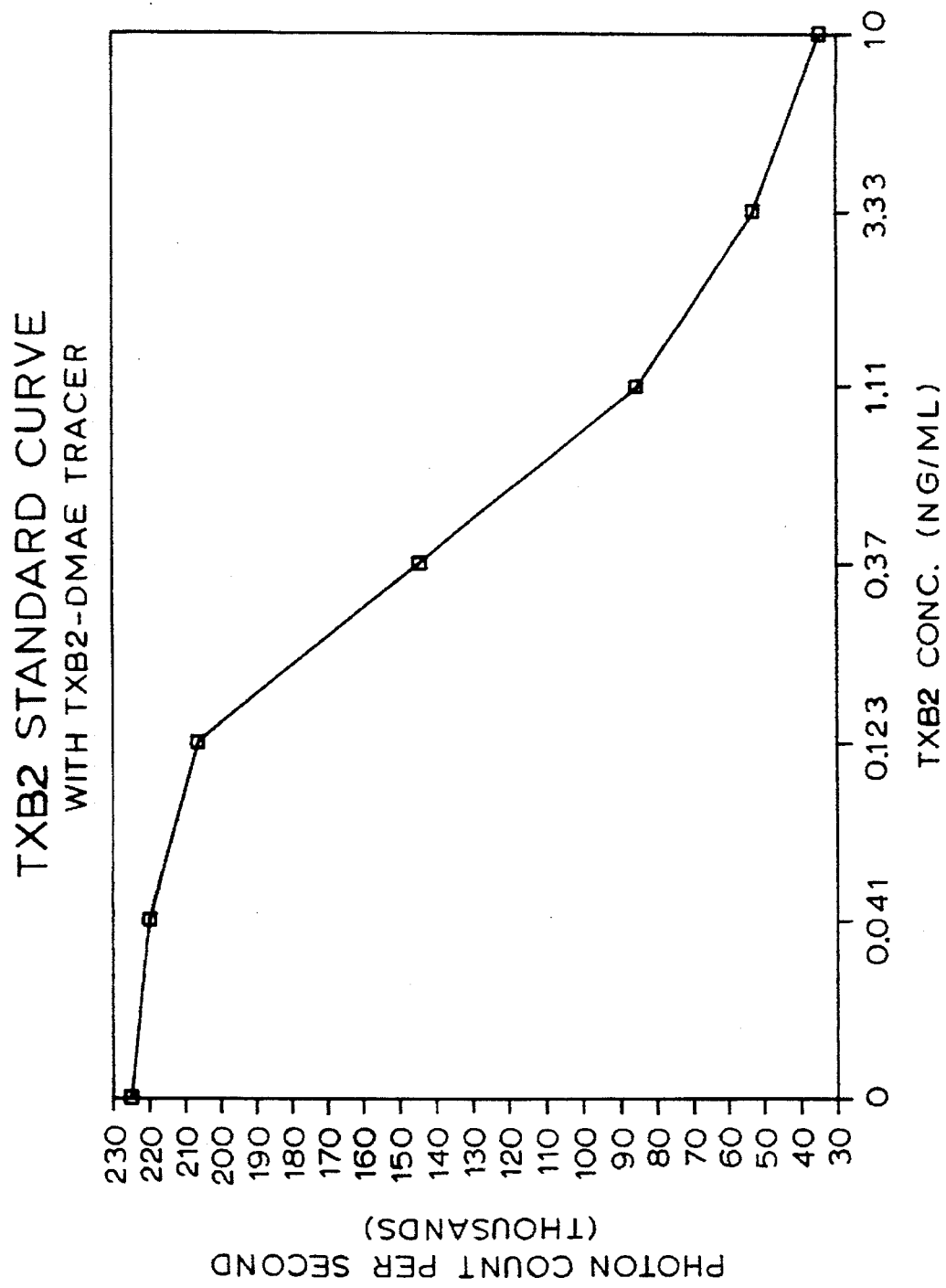

B. Assay procedure 100 ul of each of a series of $TxB_2$ standards in PBS/BSA (0–30 ng/ml) were added to polystyrene test tubes (12×75 mm, Sarstedt, West Germany). 100 ul of the tracer solution of A with a total activity of 350,000 RLU, was then added to each tube. 100 ul of rabbit anti-$TxB_2$ antiserum (prepared in A diluted 1/40000 in PBS/BSA) was pipeted into all tubes. All tubes were vortexed and incubated at room temperature for 1 hour. 500 ul of the diluted PMP suspension of A was then added to all the tubes and incubated for 45 minutes at room temperature. The PMP in the tubes were then magnetically separated from the supernatant. The supernatant was decanted and the PMP were then washed once with 500 ul of water then resuspended in 100 ul of water. The tubes were then placed in a luminometer and counted as described in Example 12B. The displacement curve in FIG. 13 shows that the photon counts were inversely proportional to the concentration of $TxB_2$ in the standards.

What is claimed is:

1. A method for preparing a conjugate of an acridinium ester and folate or a folate derivative comprising:
    A. incubating the folate or folate derivative with an amino-reactive compound to couple an acyl or alkyloxy carbonyl group to the C-2 amino group of the folate or folate derivative, to form a protected folate intermediate;
    B. activating at least one carboxylic group of the protected folate intermediate of step A;
    C. incubating the activated protected folate intermediate of step B with an acridinium ester to form an acridinium ester-protected folate intermediate conjugate; and
    D. incubating the acridinium ester-protected folate intermediate conjugate in an acidic medium for a time sufficient to remove the amino-protecting group from the C-2 amino group, to form an acridinium ester-folate conjugate or an acridinium ester-folate derivative conjugate,
    wherein the acridinium ester has the formula:

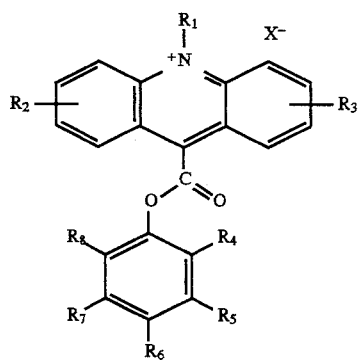

wherein:
X⁻ is an anion;

R₁ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

R₂, R₃, R₅, and R₇ are selected from the group consisting of alkoxyl, amino, halide, hydrogen, hydroxyl, nitro,

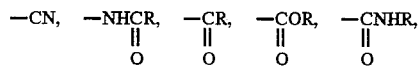

—SCN, —COOH, and —SO₃H;

R₄ and R₈ are selected from the group consisting of alkenyl, alkoxyl, alkyl, alkynyl, and aralkyl;

R₆ is selected from the group consisting of Q—R—Nu

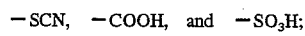

Q—R—Nu, and Q—Nu where:
Nu is a nucleophilic group;
Q is selected from the group consisting of diazo,

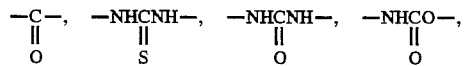

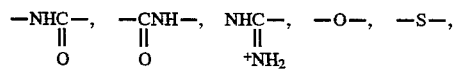

and —NH—;

and —NH—; and

I is selected from the group consisting of —SO₃H, —OSO₃H, —PO(OH)₂, —OPO(OH)₂, and —COOH;

except that, where R₆=QNu, the condition where Q=

and Nu=—OH is excluded; and

R comprises up to 20 heteroatoms and is selected from the group consisting of alkenyl, alkyl, alkynyl, aralkyl, and aryl.

2. The method of claim 1 wherein:
X⁻ is selected from the group consisting of halide, CH₃SO₄⁻, FSO₃⁻, CF₃SO₃⁻, C₄F₉SO₃⁻, and

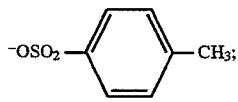

R₁ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl; and aryl;

R₂, R₃, R₅, and R₇ are selected from the group consisting of C₁–C₄ alkoxyl, amino, halide, hydrogen, hydroxyl, nitro, —CN, —SCN, —COOH, and —SO₃H;

R₄ and R₈ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

3. The method of claim 1 wherein:

$X^-$ is a halide;

$R_1$ is an alkyl comprising 1 to 10 carbon atoms;

$R_2$, $R_3$, $R_5$, and $R_7$ are selected from the group consisting of $C_1$–$C_4$ alkoxyl, amino, hydrogen, nitro, —CN, and —$SO_3H$;

$R_4$ and $R_8$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —$NO_2$, —CN, —$SO_3H$, —$N(R)_3^+$, and —$S(R)_3^+$.

4. The method of claim 1 wherein:

$X^-$ is bromide;

$R_1$ is methyl;

$R_2$, $R_3$, $R_5$, and $R_7$ are hydrogen; and $R_4$ and $R_8$ are methyl.

5. The method of claim 1 wherein $R_6$ is

6. A method for preparing a conjugate of an acridinium ester and Vitamin $B_{12}$ or a Vitamin $B_{12}$ derivative comprising:

A. incubating the Vitamin $B_{12}$ or Vitamin $B_{12}$ derivative in an acidic medium for a time sufficient to deaminate the primary propanamide side chains of the Corrin ring of the Vitamin $B_{12}$ or Vitamin $B_{12}$ derivative, to produce a mixture of carboxylated Vitamin $B_{12}$ or Vitamin $B_{12}$ derivative;

B. subjecting the mixture of carboxylated Vitamin $B_{12}$ or Vitamin $B_{12}$ derivative to HPLC to separate the tricarboxylic, the dicarboxylic, and the three monocarboxylic Vitamin $B_{12}$ or Vitamin $B_{12}$ derivative forms;

C. isolating one of the monocarboxylic Vitamin $B_{12}$ or Vitamin $B_{12}$ derivative forms;

D. activating the carboxylic group of the monocarboxylated Vitamin $B_{12}$ or Vitamin $B_{12}$ derivative of step C; and E. incubating the activated monocarboxylic Vitamin $B_{12}$ or Vitamin $B_{12}$ derivative of step D with an acridinium ester to produce an acridinium ester-Vitamin $B_{12}$ conjugate or an acridinium ester-Vitamin $B_{12}$ derivative conjugate, wherein the acridinium ester has the formula:

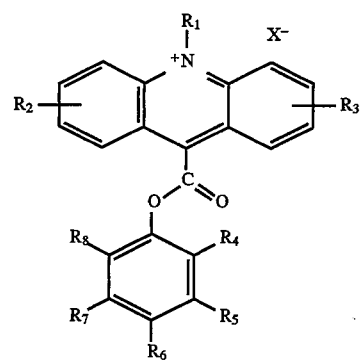

wherein:

$X^-$ is an anion;

$R_1$ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro,

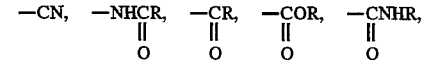

$R_4$ and $R_8$ are selected from the group consisting of alkenyl, alkoxyl, alkyl, alkynyl, and aralkyl;

$R_6$ is selected from the group consisting of Q—R—Nu,

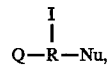

where:

Nu is a nucleophilic group;

Q is selected from the group consisting of diazo,

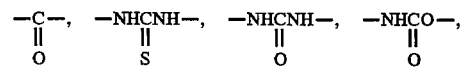

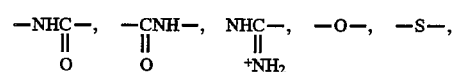

and —NH—;

and

I is selected from the group consisting of —$SO_3H$, —$OSO_3H$, —$PO(OH)_2$, —$OPO(OH)_2$, and —COOH;

except that, where $R_6$=QNu, the condition where Q=

and Nu=—OH is excluded; and

R comprises up to 20 heteroatoms and is selected from the group consisting of alkenyl, alkyl, alkynyl, aralkyl, and aryl.

7. The method of claim 6 wherein:

$X^-$ is selected from the group consisting of halide, $CH_3SO_4^-$, $FSO_3^-$, $CF_3SO_3^-$, $C_4F_9SO_3^-$, and

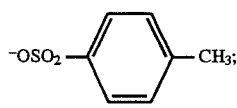

$R_1$ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

$R_2$, $R_3$, $R_5$, and $R_7$ are selected from the group consisting of $C_1$–$C_4$ alkoxyl, amino, halide, hydrogen, hydroxyl, nitro, —CN, —SCN, —COOH, and —$SO_3H$;

$R_4$ and $R_8$ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

8. The method of claim 6 wherein:

$X^-$ is a halide;

$R_1$ is an alkyl comprising 1 to 10 carbon atoms; $R_2$, $R_3$, $R_5$, and $R_7$ are selected from the group consisting of $C_1$–$C_4$ alkoxyl, amino, hydrogen, nitro, —CN, and —$SO_3H$;

$R_4$ and $R_8$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —$NO_2$, —CN, —$SO_3H$, —$N(R)_3^+$, and —$S(R)_3^+$.

9. The method of claim 6 wherein:

$X^-$ is bromide;

$R_1$ is methyl;

$R_2$, $R_3$, $R_5$, and $R_7$ are hydrogen; and $R_4$ and $R_8$ are methyl.

10. The method of claim 6 wherein $R_6$ is —CONH—$CH_2CH_2$—$NH_2$.

11. A method for preparing a conjugate of an acridinium ester and 17-beta-estradiol or a 17-beta-estradiol derivative comprising:

A. activating a functional group attached to the 17-beta-estradiol or the 17-beta-estradiol derivative, to form an activated estradiol intermediate; and B. incubating the activated estradiol intermediate with an acridinium ester to form an acridinium ester-17-beta-estradiol conjugate or an acridinium ester-17-beta-estradiol derivative conjugate, wherein the acridinium ester has the formula:

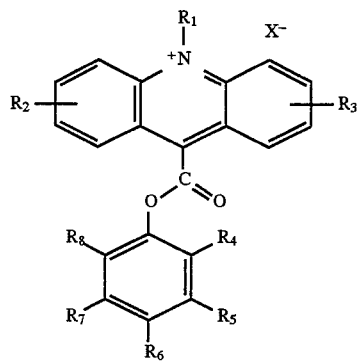

wherein:

$X^-$ is an anion;

$R_1$ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro,

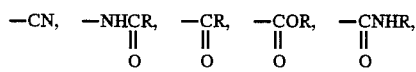

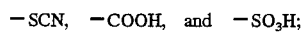

$R_4$ and $R_8$ are selected from the group consisting of alkenyl, alkoxyl, alkyl, alkynyl, and aralkyl;

$R_6$ is selected from the group consisting of Q—R—Nu,

where:

Nu is a nucleophilic group;

Q is selected from the group consisting of diazo,

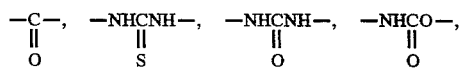

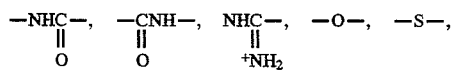

and —NH—; and

I is selected from the group consisting of —$SO_3H$, —$OSO_3H$, —$PO(OH)_2$, —$OPO(OH)_2$, and —COOH;

except that, where $R_6$=QNu, the condition where Q=

and Nu=—OH is excluded; and

R comprises up to 20 heteroatoms and is selected from the group consisting of alkenyl, alkyl, alkynyl, aralkyl, and aryl.

12. The method of claim 11 wherein:

$X^-$ is selected from the group consisting of halide, $CH_3SO_4^-$,

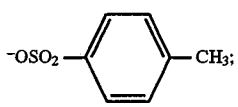

$R_1$ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

$R_2$, $R_3$, $R_5$, and $R_7$ are selected from the group consisting of $C_1$–$C_4$ alkoxyl, amino, halide, hydrogen, hydroxyl, nitro, —CN, —SCN, —COOH, and —$SO_3H$;

$R_4$ and $R_8$ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

13. The method of claim 11 wherein:

$X^-$ is a halide;

$R_1$ is an alkyl comprising 1 to 10 carbon atoms;

$R_2$, $R_3$, $R_5$, and $R_7$ are selected from the group consisting of $C_1$–$C_4$ alkoxyl, amino, hydrogen, nitro, —CN, and —$SO_3H$;

$R_4$ and $R_8$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —$NO_2$, —CN, —$SO_3H$, —$N(R)_3^-$, and —$S(R)_3^-$.

14. The method of claim 11 wherein:

$X^-$ is bromide;

$R_1$ is methyl;

$R_2$, $R_3$, $R_5$, and $R_7$ are hydrogen; and $R_4$ and $R_8$ are methyl.

15. The method of claim 11 wherein $R_6$ is —CONH—$CH_2CH_2$—$NH_2$.

16. A method for preparing a conjugate of an acridinium ester and cortisol or a cortisol derivative comprising:

A. activating a functional group attached to the cortisol or cortisol derivative, to form an activated cortisol intermediate; and B. incubating the activated cortisol intermediate with an acridinium ester to form an acridinium ester-cortisol conjugate or an acridinium ester-cortisol derivative conjugate, wherein the acridinium ester has the formula:

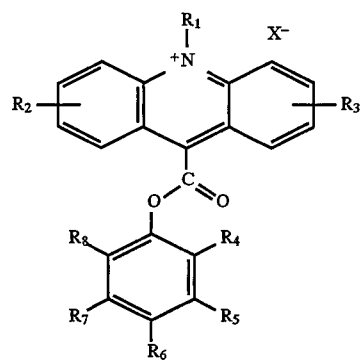

wherein:

$X^-$ is an anion;

$R_1$ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro,

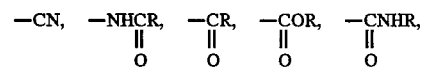

$R_4$ and $R_8$ are selected from the group consisting of alkenyl, alkoxyl, alkyl, alkynyl, and aralkyl;

$R_6$ is selected from the group consisting of Q—R—Nu

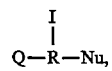

where:

Nu is a nucleophilic group;

Q is selected from the group consisting of diazo,

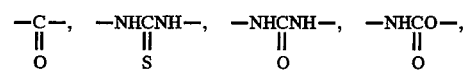

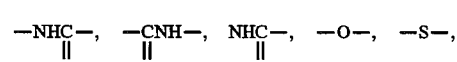

and —NH—;

and

I is selected from the group consisting of —$SO_3H$, —$OSO_3H$, —PO(OH)$_2$, —OPO(OH)$_2$, and —COOH;

except that, where $R_6$=QNu, the condition where Q=

and Nu=—OH is excluded; and

R comprises up to 20 heteroatoms and is selected from the group consisting of alkenyl, alkyl, alkynyl, aralkyl, and aryl.

17. The method of claim 16 wherein:

X⁻ is selected from the group consisting of halide, $CH_3SO_4^-$, $FSO_3^-$, $CF_3SO_3^-$, $C_4F_9SO_3^-$, and

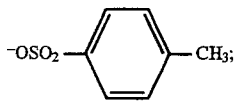

$R_1$ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

$R_2$, $R_3$, $R_5$, and $R_7$ are selected from the group consisting of $C_1$-$C_4$ alkoxyl, amino, halide, hydrogen, hydroxyl, nitro, —CN, —SCN, —COOH, and —$SO_3H$;

$R_4$ and $R_8$ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

18. The method of claim 16 wherein:

X⁻ is a halide;

$R_1$ is an alkyl comprising 1 to 10 carbon atoms;

$R_2$, $R_3$, $R_5$, and $R_7$ are selected from the group consisting of $C_1$-$C_4$ alkoxyl, amino, hydrogen, nitro, —CN, and —$SO_3H$;

$R_4$ and $R_8$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —NO=, —CN, —$SO_3H$, —$N(R)_3^+$, and —$S(R)_3^+$.

19. The method of claim 16 wherein:

X⁻ is bromide;

$R_1$ is methyl;

$R_2$, $R_3$, $R_5$, and $R_7$ are hydrogen; and $R_4$ and $R_8$ are methyl.

20. The method of claim 16 wherein $R_6$ is —COHN—$CH_2CH_2$—$NH_2$.

21. A method for preparing a conjugate of an acridinium ester and a prostaglandin or a prostaglandin analog comprising:

A. activating the terminal carboxylic group of the prostaglandin or prostaglandin analog; to form an activated intermediate of the prostaglandin or the prostaglandin analog; and B. incubating the activated intermediate with an acridinium ester to form an acridinium ester-prostaglandin conjugate or acridinium ester-prostaglandin analog conjugate, wherein the acridinium ester has the formula:

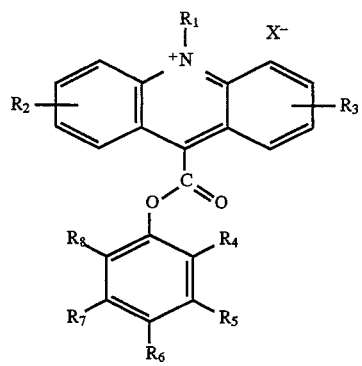

wherein:

X⁻ is an anion;

$R_1$ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro, $$-CN, \quad -\underset{\underset{O}{\|}}{N}HCR, \quad -\underset{\underset{O}{\|}}{C}R, \quad -\underset{\underset{O}{\|}}{C}OR, \quad -\underset{\underset{O}{\|}}{C}NHR,$$

—SCN, —COOH, and —$SO_3H$;

$R_4$ and $R_8$ are selected from the group consisting of alkenyl, alkoxyl, alkyl, alkynyl, and aralkyl;

$R_6$ is selected from the group consisting of Q—R—Nu,

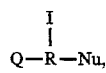

where:

Nu is a nucleophilic group;

Q is selected from the group consisting of diazo,

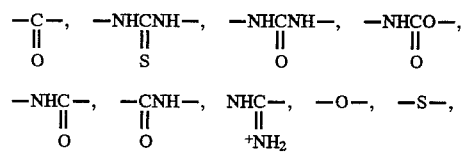

and —NH—;

and

I is selected from the group consisting of —$SO_3H$, —$OSO_3H$, —$PO(OH)_2$, —$OPO(OH)_2$, and —COOH;

except that, where $R_6$=QNu, the condition where Q=

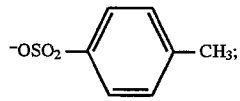

and Nu=—OH is excluded; and

R comprises up to 20 heteroatoms and is selected from the group consisting of alkenyl, alkyl, alkynyl, aralkyl, and aryl.

22. The method of claim 21 wherein:

$X^-$ is selected from the group consisting of halide, $CH_3SO_4^-$, $-OSO_2-\text{C}_6\text{H}_4-CH_3$;

$R_1$ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

$R_2$, $R_3$, $R_5$, and $R_7$ are selected from the group consisting of $C_1$–$C_4$ alkoxyl, amino, halide, hydrogen, hydroxyl, nitro, —CN, —SCN, —COOH, and —SO$_3$H;

$R_4$ and $R_8$ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

23. The method of claim 21 wherein:

$X^-$ is a halide;

$R_1$ is an alkyl comprising 1 to 10 carbon atoms;

$R_2$, $R_3$, $R_5$, and $R_7$ are selected from the group consisting of $C_1$–$C_4$ alkoxyl, amino, hydrogen, nitro, —CN, and —SO$_3$H;

$R_4$ and $R_5$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —NO$_2$, —CN, —SO$_3$H, —N(R)$_3^+$, and —S(R)$_3^+$.

24. The method of claim 21 wherein:

$X^-$ is bromide;

$R_1$ is methyl;

$R_2$, $R_3$, $R_5$, and $R_7$ are hydrogen; and $R_4$ and $R_8$ are methyl.

25. The method of claim 21 wherein $R_6$ is —CONH—CH$_2$CH$_2$—NH$_2$.

26. The method of claim 21, 22, 23, 24, or 25 wherein the prostaglandin is thromboxane B$_2$.

27. A method for preparing a conjugate of a specific binding member and an acridinium ester comprising:

A. providing an acridinium ester;

B. providing a specific binding member which comprises at least one functional group capable of binding to the acridinium ester; and C. reacting the acridinium ester with the specific binding member, wherein the acridinium ester has the formula:

[Structural formula of acridinium ester with substituents $R_1$, $R_2$, $R_3$, $R_4$, $R_5$, $R_6$, $R_7$, $R_8$, $X^-$]

wherein:

$X^-$ is an anion;

$R_1$ is (a) attached to the ring nitrogen of the acridine nucleus of the acridinium ester through a carbon, (b) comprises up to 20 heteroatoms, and, (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro, $$-CN, \quad -\underset{\underset{O}{\|}}{N}HCR, \quad -\underset{\underset{O}{\|}}{C}R, \quad -\underset{\underset{O}{\|}}{C}OR, \quad -\underset{\underset{O}{\|}}{C}NHR,$$

—SCN, —COOH, and —SO$_3$H;

$R_4$ and $R_8$ are selected from the group consisting of alkenyl, alkoxyl, alkyl, alkynyl, and aralkyl;

$R_6$ is selected from the group consisting of Q—R—Nu, $$\underset{|}{\overset{I}{|}} \\ Q-R-Nu,$$

and Q—Nu where:

Nu is a nucleophilic group;

Q is selected from the group consisting of diazo, $$-\underset{\underset{O}{\|}}{C}-, \quad -\underset{\underset{S}{\|}}{N}HCNH-, \quad -\underset{\underset{O}{\|}}{N}HCNH-, \quad -\underset{\underset{O}{\|}}{N}HCO-,$$

$$-\underset{\underset{O}{\|}}{N}HC-, \quad -\underset{\underset{O}{\|}}{C}NH-, \quad \underset{\underset{+NH_2}{\|}}{N}HC-, \quad -O-, \quad -S-,$$

and —NH—;

and

I is selected from the group consisting of —SO$_3$H, —OSO$_3$H, —PO(OH)$_2$, —OPO(OH)$_2$, and —COOH;

except that, where $R_6$=QNu, the condition where Q=

$$-\underset{\underset{O}{\|}}{C}-$$

and Nu=—OH is excluded; and

R comprises up to 20 heteroatoms and is selected from the group consisting of alkenyl, alkyl, alkynyl, aralkyl, and aryl.

28. The method of claim 27 wherein:

$X^-$ is selected from the group consisting of halide, $CH_3SO_4^-$, $FSO_3^-$, $CF_3SO_3^-$, $C_4F_9SO_3^-$, and

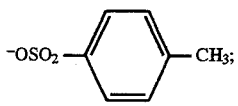

$R_1$ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

$R_2$, $R_3$, $R_5$, and $R_7$ are selected from the group consisting of $C_1$–$C_4$ alkoxyl, amino, halide, hydrogen, hydroxyl, nitro, —CN, —SCN, —COOH, and —$SO_3H$;

$R_4$ and $R_8$ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

29. The method of claim 27 wherein:

$X^-$ is a halide;

$R_1$ is an alkyl comprising 1 to 10 carbon atoms;

$R_2$, $R_3$, $R_5$, and $R_7$ are selected from the group consisting of $C_1$–$C_4$ alkoxyl, amino; hydrogen, nitro, —CN, and —$SO_3H$;

$R_4$ and $R_8$ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —$NO_2$, —CN, —$SO_3H$, —$N(R)_3^+$, and —$S(R)_3^-$.

30. The method of claim 27 wherein:

$X^-$ is bromide;

$R_1$ is methyl;

$R_2$, $R_3$, $R_5$, and $R_7$ are hydrogen; and $R_4$ and $R_8$ are methyl.

31. The method of claim 27 wherein $R_6$ is —CONH—$CH_2CH_2$—$NH_2$.

32. The method of claim 27 wherein $R_6$ is

33. The method of claim 27, 28, 29, 30, 31, or 32 wherein, in step C, the acridinium ester is reacted directly with the specific binding member.

34. The method of claim 33 wherein Nu is an amino group and the at least one functional group of the specific binding member comprises a halide, isocyanate, or thioisocyanate group which reacts directly with the amino group.

35. The method of claim 33 wherein Nu is an amino group and the at least one functional group of the specific binding member comprises a ketone or aldehyde group which reacts directly with the amino group.

36. The method of claim 35 including the additional step of reacting the reaction product of step C with a hydride reducing agent.

37. The method of claim 33 wherein Nu is a sulfhydryl group and the at least one functional group of the specific binding member comprises a thiol (sulfhydryl)-reactive group which reacts directly with the sulfhydryl group.

38. The method of claim 33 wherein Nu is a hydroxyl group and the at least one functional group of the specific binding member comprises an oxirane group which reacts directly with the hydroxyl group.

39. The method of claim 33 wherein Nu is an organometallic moiety and the at least one functional group of the specific binding member comprises a ketone or aldehyde functional group which reacts directly with the organometallic moiety.

40. The method of claim 27, 28, 29, 30, 31, or 32 wherein, in step C, the specific binding member is activated before being reacted with the acridinium ester.

41. The method of claim 40 wherein Nu is an amino group and the at least one functional group of the specific binding member comprises a carboxylic group which is activated to form an active ester before being reacted with the amino group.

42. The method of claim 27, 28, 29, 30, 31, or 32 wherein the specific binding member is selected from the group consisting of an analyte, an analyte analog and a complementary binder which specifically binds to or hybridizes to both the analyte and the analyte analog.

43. The method of claim 42 wherein the specific binding member is an antigen, a hapten, or a ligand.

44. The method of claim 42 wherein the specific binding member is a protein, a nucleic acid, or a molecule comprising nucleic acids.

45. A luminescent conjugate comprising an acridinium ester bound to a specific binding member where the acridinium ester has the formula:

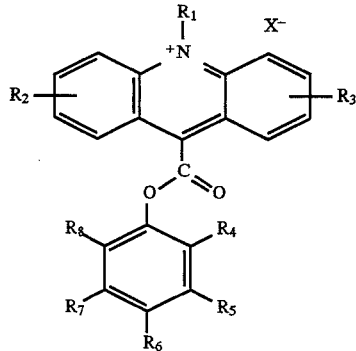

wherein:

$X^-$ is an anion;

$R_1$ is (a) attached to the ring nitrogen of the acridine nucleus of the acridinium ester through a carbon, (b) comprises up to 20 heteroatoms, and (c) is selected from the group consisting of alkenyl, alkyl, alkynyl, aralkyl, and aryl;

$R_2$, $R_3$, $R_5$, and $R_7$ are selected from the group consisting of alkoxyl, amino, halide, hydrogen, hydroxyl, nitro,

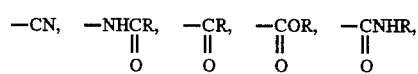

—SCN, —COOH, and —SO₃H;

R₄ and R₈ are selected from the group consisting of alkenyl, alkoxyl, alkyl, alkynyl, and aralkyl;

R₆ is selected from the group consisting of Q—R—Nu,

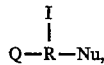

and Q—Nu
where:

Nu is a nucleophilic group;

Q is selected from the group consisting of —O— and —S—; and

I is selected from the group consisting of —SO₃H, —OSO₃H, —PO(OH)₂, —OPO(OH)₂, and —COOH; and R comprises up to 20 heteroatoms and is selected from the group consisting of alkenyl, alkyl, alkynyl, aralkyl, and aryl.

46. The luminescent conjugate of claim 45 wherein:

X⁻ is selected from the group consisting of halide, CH₃SO₄⁻, FSO₃⁻, CF₃SO₃⁻, C₄F₉SO₃⁻, and

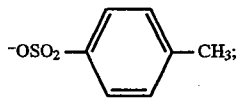

R₁ (a) comprises 1 to 24 carbon atoms, (b) comprises up to 20 heteroatoms selected from the group consisting of nitrogen, oxygen, phosphorous, and sulfur, and (c) is selected from the group consisting of alkenyl, alkyl, alkynyl, and aryl;

R₂, R₃, R₅, and R₇ are selected from the group consisting of C₁–C₄ alkoxyl, amino, halide, hydrogen, hydroxyl, nitro, —CN, —SCN, —COOH, and —SO₃H;

R₄ and R₈ are (a) selected from the group consisting of alkenyl, alkoxyl, alkyl, and alkynyl, and (b) comprise 1 to 8 carbon atoms;

Nu is selected from the group consisting of an amino group, a hydroxyl group, a sulfhydryl group, an organometallic moiety, and an active methylene group; and R (a) comprises 1 to 24 carbon atoms, and (b) comprises up to 20 heteroatoms selected from the group consisting of nitrogen, oxygen, phosphorous, and sulfur.

47. The luminescent conjugate of claim 45 wherein:

X⁻ is a halide;

R₁ is an alkyl comprising 1 to 10 carbon atoms;

R₂, R₃, R₅, and R₇ are selected from the group consisting of C₁–C₄ alkoxyl, amino, hydrogen, nitro, —CN, and —SO₃H;

R₄ and R₈ are an alkyl comprising 1 to 4 carbon atoms; and

Nu is selected from the group consisting of an amino group, a hydroxyl group, a sulfhydryl group, an organometallic moiety selected from the group consisting of Grignard reagents, lithium compounds, and phenylsodium, and an active methylene group adjacent to a strong electron-withdrawing group selected from the group consisting of —NO₂, —CN, —SO₃H, —N(R)₃⁺, and —S(R)₃⁺.

48. The luminescent conjugate of claim 45 wherein:

X⁻ is bromide;

R₁ is methyl;

R₂, R₃, R₅, and R₇ are hydrogen; and

R₄ and R₈ are methyl.

49. The luminescent conjugate of claim 45 wherein R₆ is —CONH—CH₂CH₂—NH₂.

50. The luminescent conjugate of claim 45 wherein R₆ is

51. The luminescent conjugate of claim 45, 46, 47, 48, 49, or 50 wherein the specific binding member is selected from the group consisting of an analyte, an analyte analog and a complementary binder which specifically binds to or hybridizes to both the analyte and the analyte analog.

52. The luminescent conjugate of claim 51 wherein the specific binding member is an antigen, a hapten, or a ligand.

53. The luminescent conjugate of claim 51 wherein the specific binding member is a protein, a nucleic acid, or a molecule comprising nucleic acids.

* * * * *